(12) United States Patent
Kühn et al.

(10) Patent No.: US 11,992,190 B2
(45) Date of Patent: May 28, 2024

(54) FLEXIBLE ENDOSCOPE BASED UPON AN INVESTMENT COMPOSITION

(71) Applicant: SCHOLLY FIBEROPTIC GMBH, Denzlingen (DE)

(72) Inventors: Matthias Kühn, Freiburg (DE); Stefan Schröer, Freiburg (DE); Michael Schwärzle, Freiburg (DE); Johannes Bourbon, Freiburg (DE); Lutz Labusch, Emmendingen (DE); Erwin Streck, Donaueschingen (DE); Holger Reinecke, Emmendingen (DE)

(73) Assignee: SCHÖLLY FIBEROPTIC GMBH, Denzlingen (DE)

( * ) Notice: Subject to any disclaimer, the term of this patent is extended or adjusted under 35 U.S.C. 154(b) by 0 days.

(21) Appl. No.: 17/237,280

(22) Filed: Apr. 22, 2021

(65) Prior Publication Data
US 2021/0330175 A1    Oct. 28, 2021

(30) Foreign Application Priority Data

Apr. 27, 2020    (DE) .......................... 102020111455.9

(51) Int. Cl.
*A61B 1/005*    (2006.01)
*A61B 1/00*    (2006.01)
(Continued)

(52) U.S. Cl.
CPC ........ *A61B 1/0057* (2013.01); *A61B 1/00096* (2013.01); *A61B 1/0011* (2013.01);
(Continued)

(58) Field of Classification Search
CPC ... A61B 1/00096; A61B 1/0011; A61B 1/005; A61B 1/0051; A61B 1/0052;
(Continued)

(56) References Cited

U.S. PATENT DOCUMENTS 4,846,573 A * 7/1989 Taylor .................. A61B 1/0055
356/241.4
4,918,521 A * 4/1990 Yabe .................. A61B 1/00177
600/109

(Continued)

FOREIGN PATENT DOCUMENTS

WO    9713452 A1    4/1997
WO    2019002186 A1    3/2019
(Continued)

OTHER PUBLICATIONS

Office Action and References cited issued for U.S. Appl. No. 17/237,280.
(Continued)

*Primary Examiner* — Aaron B Fairchild
*Assistant Examiner* — Stephen Floyd London
(74) *Attorney, Agent, or Firm* — Grogan, Tuccillo & Vanderleeden LLP

(57) ABSTRACT

A flexible endoscope for insertion into the human body includes a flexible section arranged in a distal end region of the endoscope. The endoscope further includes a tip segment distally adjoining the flexible section, the tip segment being controllable by at least one tension cord. The flexible section is formed by means of an investment composition that is mechanically anchored to the tip segment and/or a proximal counter bearing, and the investment compound is elastically deformable.

15 Claims, 16 Drawing Sheets

(51) Int. Cl.
*A61B 1/05* (2006.01)
*A61B 1/06* (2006.01)
*A61B 1/07* (2006.01)

(52) U.S. Cl.
CPC .............. *A61B 1/05* (2013.01); *A61B 1/0684* (2013.01); *A61B 1/07* (2013.01); *A61B 2562/028* (2013.01); *A61B 2562/0285* (2013.01)

(58) Field of Classification Search
CPC ... A61B 1/0053; A61B 1/0055; A61B 1/0056; A61B 1/0057; A61B 1/008; A61B 1/051; A61B 1/053; A61B 1/0676; A61M 25/0133; A61M 25/0136; A61M 25/0138; A61M 25/0141; A61M 25/0144; A61M 25/0147; A61M 25/0152; A61M 25/0155; A61M 25/0158; A61M 2025/015; A61M 2025/0161; A61M 2025/0163
USPC .................................................. 600/140, 141
See application file for complete search history.

(56) References Cited

U.S. PATENT DOCUMENTS

| | | | | |
|---|---|---|---|---|
| 5,089,895 | A * | 2/1992 | Fraker | G08B 13/19619 348/E5.026 |
| 6,491,626 | B1 | 12/2002 | Stone et al. | |
| 2006/0167340 | A1 * | 7/2006 | Pease | A61B 1/00052 600/109 |
| 2007/0129466 | A1 * | 6/2007 | Kagawa | B82Y 30/00 523/468 |
| 2008/0287741 | A1 | 11/2008 | Ostrovsky | |
| 2009/0093679 | A1 | 4/2009 | Suigetsu | |
| 2009/0137875 | A1 | 5/2009 | Kitagawa et al. | |
| 2009/0253963 | A1 * | 10/2009 | Suigetsu | A61B 1/0055 425/446 |
| 2010/0160735 | A1 | 6/2010 | Bakos | |
| 2010/0217082 | A1 | 8/2010 | Ito et al. | |
| 2011/0106101 | A1 * | 5/2011 | Tortonese | A61M 25/0147 606/129 |
| 2011/0288372 | A1 * | 11/2011 | Petersen | A61B 1/00066 600/109 |
| 2012/0071864 | A1 | 3/2012 | Banju et al. | |
| 2012/0238805 | A1 | 9/2012 | Iwasaka | |
| 2012/0245418 | A1 | 9/2012 | Boulais | |
| 2013/0041223 | A1 * | 2/2013 | Kato | A61B 1/0051 600/121 |
| 2013/0281779 | A1 * | 10/2013 | Robertson | A61B 1/0669 600/109 |
| 2016/0235274 | A1 | 8/2016 | Graham | |
| 2016/0317220 | A1 | 11/2016 | Guo | |
| 2018/0289242 | A1 * | 10/2018 | Dai | A61B 1/0055 |
| 2018/0303325 | A1 * | 10/2018 | Fujimori | A61B 1/0011 |
| 2019/0175869 | A1 | 6/2019 | Kirt et al. | |
| 2020/0100662 | A1 * | 4/2020 | Jensen | A61B 1/0011 |
| 2020/0113415 | A1 | 4/2020 | Kristensen | |
| 2020/0297193 | A1 * | 9/2020 | Takahashi | H04N 23/51 |
| 2021/0038209 | A1 | 2/2021 | Grüner et al. | |
| 2021/0068642 | A1 * | 3/2021 | Sorenson | B29C 45/14467 |
| 2021/0228064 | A1 * | 7/2021 | Sorenson | A61B 1/005 |

FOREIGN PATENT DOCUMENTS

WO  2020070851 A1  4/2020
WO  2021219180     11/2021

OTHER PUBLICATIONS

United States Office Action and list of Examiner cited references dated Feb. 14, 2023 from corresponding U.S. Appl. No. 17/237,332.
United States Office Action and list of Examiner cited references dated Aug. 19, 2022 from corresponding U.S. Appl. No. 17/237,332.

* cited by examiner

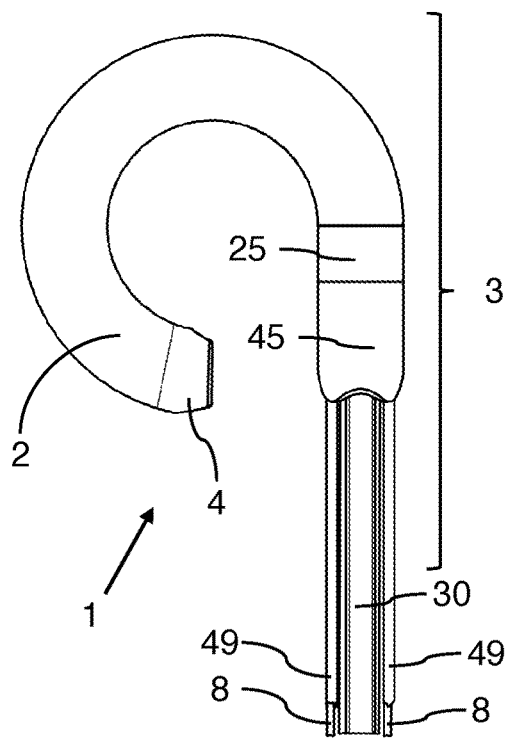
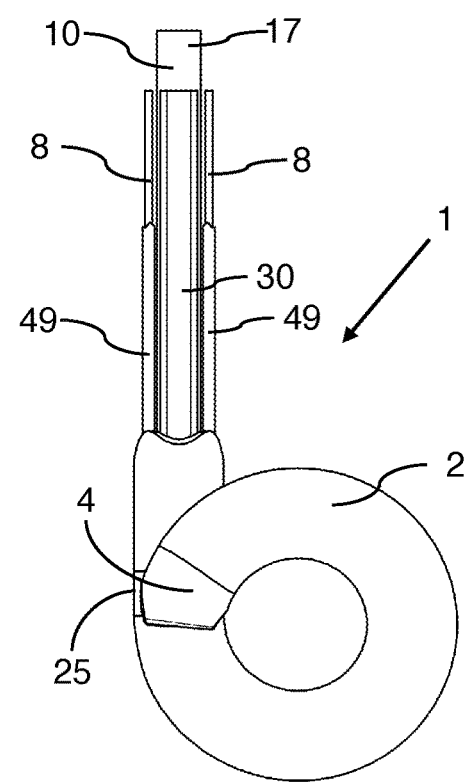
Fig. 1          Fig. 2
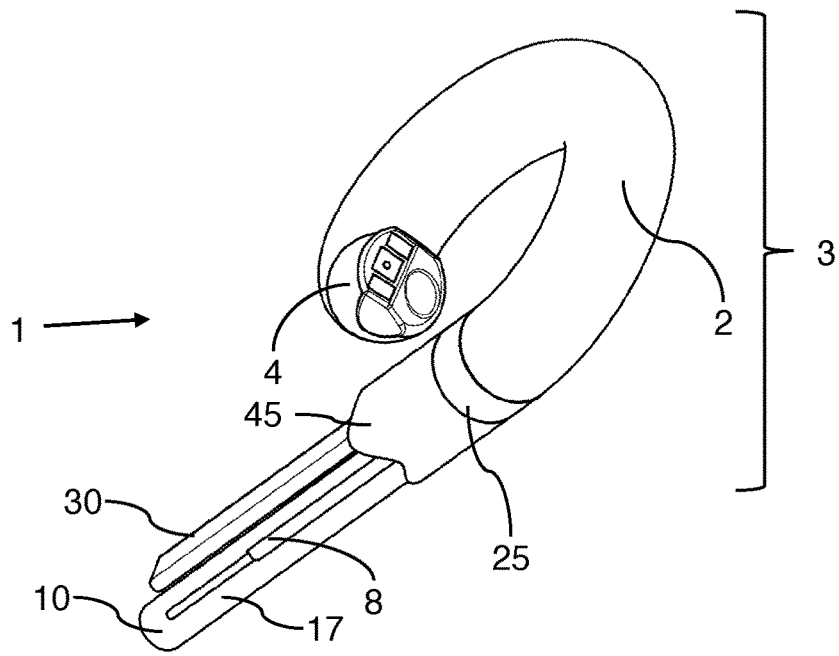
Fig.3

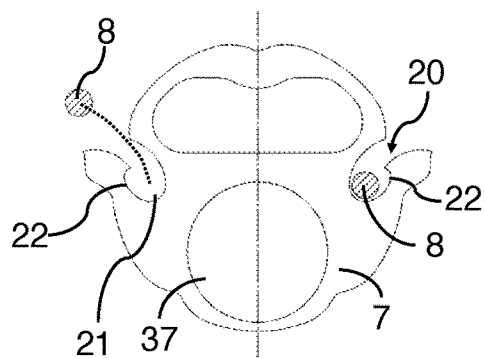
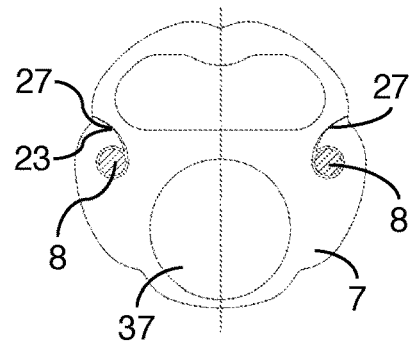
Fig. 32  Fig. 33
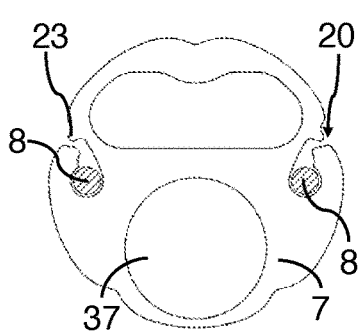
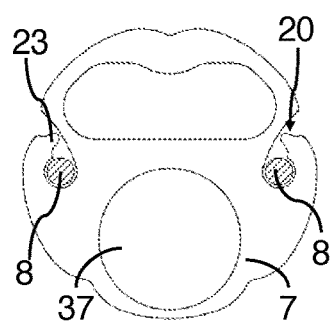
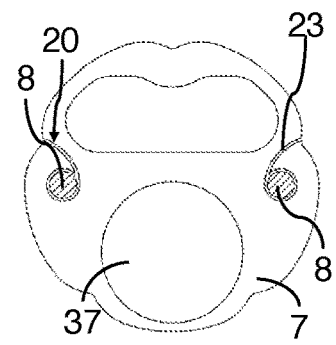
Fig. 34  Fig. 35  Fig. 36
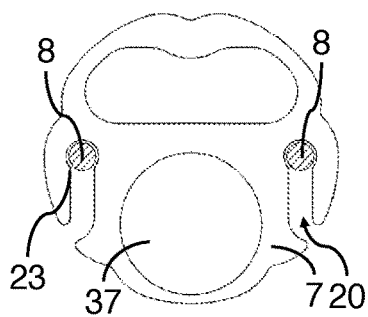
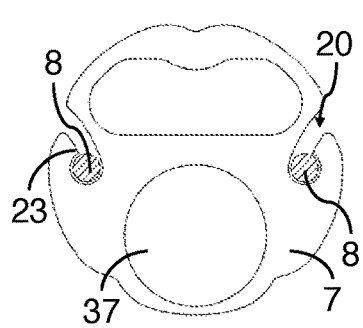
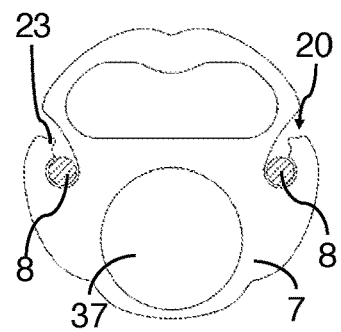
Fig. 37  Fig. 38  Fig. 39
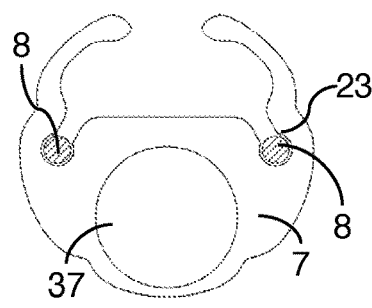
Fig. 40

FLEXIBLE ENDOSCOPE BASED UPON AN INVESTMENT COMPOSITION

CROSS-REFERENCE TO RELATED APPLICATIONS

This application claims priority to German Patent Application No. 102020111455.9, filed on Apr. 27, 2020, which is herein incorporated by reference in its entirety.

FIELD OF THE INVENTION

The invention relates to a flexible endoscope with a flexible section, which is arranged in a distal end region of the endoscope, and with a tip segment distally adjoining the flexible section, said tip segment being controllable by means of at least one tension cord.

The invention further relates to a production or assembly method for such an endoscope.

Endoscopes as described above are available on the market in many ways and are used in particular for medical interventions; that is to say, such endoscopes can in particular be designed in order to meet legal requirements so that they can be used for insertion into the human body.

There do currently exist very powerful endoscopes with controllable tip segments. However, these are very expensive to produce and are therefore only suitable for frequent reuse. For a wide variety of reasons, however, there is also a need for the endoscopes described above for single-use applications; that is to say, for applications in which the endoscope is only to be used once for a medical intervention and therefore, in particular, does not have to be sterilizable. In order to be able to produce such endoscopes at reasonable costs, which is essential if they are for single use, various approaches have been pursued. However, resorting to cheap elastomer materials often leads to inadequate performance of the endoscopes with regard to their mechanical properties; in particular, the controllability of such endoscopes suffers. In addition, it is difficult to be able to offer sufficient functionality for a single-use endoscope in case of a tight production budget.

BACKGROUND OF THE INVENTION

Proceeding from this background, the invention is based upon the problem of providing a flexible endoscope that can be produced easily and inexpensively, but at the same time has high mechanical stability, good controllability, and high functionality. For simple production, a small number of built-in individual parts of the endoscope is also desired.

SUMMARY OF THE INVENTION

In order to solve this problem in a flexible endoscope, the features of claim 1 are provided according to the invention. In particular, according to the invention, in order to solve the problem in a flexible endoscope of the type mentioned above, it is proposed that the flexible section be formed by means of an investment composition and that the investment composition be mechanically anchored in the tip segment and/or a proximal counter bearing. In this way, it can be achieved in particular that the investment composition, which also forms the flexible section of the endoscope, also forms the tip segment, in order to take over a wide range of functions there, as will be explained below in further detail.

The advantage of this embodiment is that, even in the case of very small curvature radii, as can occur with extreme actuation of the flexible region, a detachment of the investment composition from the distal/proximal counter bearing can be effectively prevented by the mechanical anchoring.

This is especially true when very soft elastomer materials such as silicone or materials with poor adhesive properties are used as the investment composition.

The tip segment of the endoscope, in particular a rigid carrier body within the tip segment, can thus form a distal counter bearing for the flexible section and, in particular, the tension cords, or can be understood as such. For this purpose, the tip segment can have, in particular, a rigid carrier body which serves as a distal counter bearing and provides distal anchoring aids for this purpose.

The flexible section is preferably arranged between the tip segment and the proximal counter bearing or connects the tip segment to the proximal counter bearing. In other words, the proximal counter bearing can thus directly adjoin the flexible section of the endoscope.

In order to enable a particularly robust anchoring of the investment composition, it is also proposed that the distal tip segment form a proximal end surface and that the investment composition extend distally beyond this proximal end surface. This end surface can be formed, for example, by a carrier body of the tip segment. In addition or as an alternative, it is further proposed that the proximal counter bearing form a distal end surface and that the investment composition extend proximally beyond the distal end surface.

For a robust anchoring, it is further advantageous when the tip segment, for example a carrier body of the tip segment, forms a distal anchoring aid for anchoring the investment composition in the distal tip segment. It is equally advantageous when the proximal counter bearing forms a proximal anchoring aid for anchoring the investment composition in the proximal counter bearing.

Both the distal and the proximal anchoring aid can be designed in various ways. For example, they can be realized by means of a surface treatment and/or by means of an adhesion agent layer. Furthermore, they can also be realized by interlocking structures such as depressions, gouges, transverse holes, through-holes, or blind holes (in particular formed on the aforementioned carrier body). Combinations of these means can also be implemented in order to achieve the desired anchoring aid Interlocking structures can in particular be designed in such a way that they provide mechanical, in particular form-fitting, anchoring of the investment composition. For this purpose, it is particularly advantageous when the respective proximal/distal counter bearing is at least partially produced by means of an additive production process, because, as a result, straight gouges as interlocking structures can be produced particularly easily.

The advantage of the design of the anchoring aids is that tensile and compressive forces, which act in the respective interface between the respective counter bearing and the investment composition, can be better absorbed and dissipated. In particular, a detachment of the investment composition from the respective counter bearing can thus be effectively prevented.

If the investment composition is formed by means of a casting or injection molding process or introduced into the endoscope, then the investment composition can completely fill the interlocking structures. As a result, an existing adhesive surface between the respective counter bearing and the investment composition can be enlarged. In addition, this enables a mechanical interlocking to be achieved between the interlocking structures and the investment composition; this interlocking can absorb transverse forces.

One possible embodiment thus provides for the use of an injection molding process for introducing the investment composition. In this case, the investment composition is an injection molding composition. Other possible investment methods are hot stamping, injection stamping, or 3D printing.

In general, it is preferred when preferably all internal components of the flexible section are at least partially invested in the investment composition and are thus held in position. Such components of the flexible section can be, in particular: tension cords, guide elements, electrical lines such as power supply lines or data/signal lines, optical fibers, etc.

It is further preferred for the investment composition to form a continuous connection which extends over the entire flexible section formed by the investment composition.

The proximal counter bearing can be mounted onto or inserted into a longitudinally and/or torsionally rigid proximal stabilization tube, which can extend up to a proximal end region of the endoscope. In the proximal stabilization tube, the at least one tension cord can be guided up to a proximal end of the endoscope. The at least one tension cord can further preferably be passed through the proximal counter bearing. As a result, adjustment forces can be exerted particularly reliably on the distal tip segment and thus on the flexible section, in each case relative to the counter bearing.

When controlling the tip segment with the aid of the at least one tension cord, the proximal counter bearing can thus remain statically in space, in particular supported upon or held by the proximal stabilization tube. This enables a defined bending of the flexible section relative to the proximal counter bearing by means of the at least one tension cord According to a further aspect of possibly independent inventive quality, the investment composition can be used, in particular in combination with a skeleton of guide elements, not only in order to achieve a high degree of mobility of the flexible section of the endoscope; rather, the investment composition can also be used in order to invest electronic functional elements that are arranged in the tip segment In other words, the distal tip segment can accordingly have at least one electronic, in particular optoelectronic, functional element; that is to say, for example, a light source, an image sensor, or some other sensor. This functional element can now preferably be invested in the investment composition and thus fixed. In the production of the endoscope, this approach has the advantage that individual assembly and production steps can be omitted It is particularly preferable here for the investment composition to extend without interruption from the tip segment into the flexible region, because, in this case, the investment composition can be introduced especially easily into the endoscope, more precisely into the endoscope tip, in a casting or injection molding process, in particular by injection molding or vacuum casting, in such a way that the investment composition fulfills its desired function in the distal tip segment as well as in the flexible region of the endoscope. The distal counter bearing provided by the tip segment can be completely or partially enclosed by the investment composition The vacuum casting process offers the advantage that even the smallest cavities can be filled with the investment composition without trapping air. An advantage of using the investment composition in the tip segment, in addition to the fixing of filigree electronic components in desired positions and/or orientations within the tip segment, is that air pockets can also be avoided, especially when using the vacuum casting process. This can be decisive in order to be able to better dissipate heat loss from these components/functional elements.

In addition, the investment composition can act as an optical element in the region of the tip segment. For example, the investment composition can be chosen such that it transmits light or allows light to pass, but scatters it, for example in order to enable diffuse illumination by means of a commercially available LED (which typically does not offer diffuse illumination)

Functional elements as mentioned above can be, for example: Sensors (image/temperature/pressure/pH value/magnetic field/position/reference sensors), light sources (LEDs, lasers, monochromatic, polychromatic/multispectral), active optics (scan mirrors, tunable lenses, etc.).

The investment composition can therefore also be used in order to invest optical components such as, for example, illuminating light fibers, image guide fibers, diffractive and/or refractive optics in the region of the tip segment.

According to a further embodiment, it can also be provided that the investment composition forms such an optical element, for example a diffusing screen or refractive or diffractive optics, in the tip segment. For this purpose, the optical component can be formed during the production of the endoscope, in particular, by making an impression of the investment composition from a master structure.

More precisely, it can be provided in particular that the investment composition forms an optical beam-shaping element for the shaping of beams of illuminating light emitted by the endoscope. For this purpose, the investment composition can be shaped, in particular, from a micro/nanostructure in the region of the optical beam-shaping element. Such optical beam shaping elements can be, for example, refractive lenses or diffractive lenses, also Fresnel lenses, or diffractive optical elements (DOEs) for generating structured lighting. Such elements can be obtained in a manner known per se by making impressions of said micro/nanostructures.

According to a particularly preferred embodiment, at least one light source, preferably in the form of an LED, is invested into the investment composition in the region of the tip segment in such a way that the investment composition serves as an optical fiber and diffuser for the light source. The advantage of this embodiment is that separate optical components, such as optical fibers or diffusers to improve the radiation characteristics of the light source, can be omitted. In particular, homogeneous illumination of a distal observation region of the endoscope can thereby be achieved in a particularly simple manner.

The investment composition can also be used in order to invest optical fibers in the distal tip segment, wherein these optical fibers transport light from the proximal region of the endoscope to the distal end of the endoscope. In this case, the light source can be located in the proximal endoscope region (for example in a handle of the endoscope), or it can be an external light source that is connected to the endoscope.

It can thus be provided that light is received and/or emitted by an electronic component (such as the one mentioned above) through the investment composition. It should be noted that the investment composition can simultaneously be used in order to form the flexible region of the endoscope.

In other embodiments of the endoscope, an optical end surface, in particular configured as a flat surface, can also be configured on the distal tip segment, which is not encased by the investment composition. In this case, the light received and/or emitted by the endoscope cannot be transmitted through the investment composition, but rather through this optical end surface.

The embodiments explained above have the advantage that additional encapsulation elements for the electronic functional element can be omitted, which greatly simplifies the assembly of the endoscope, because, in particular, entire production steps can be spared. In addition, the investment composition can take on an optical function, such as beam shaping, light scattering, or light refraction and, at the same time, ensure high mobility of the flexible region of the endoscope. Because, for this purpose, the investment composition can be introduced into the endoscope, more precisely into the endoscope tip, in a single process step, the production of the endoscope becomes simpler and therefore more cost-effective overall.

It can thus be provided in particular that several functional elements, in particular in the form of electronic and/or optical components, are inserted into the tip segment and that these functional elements are each at least partially invested into the investment composition.

The tip segment itself can have a base body which serves as a distal counter bearing for the at least one tension cord. This base body can be designed, for example, as an injection molded part. It is further preferred for the base body to have a higher rigidity than the investment composition. In this case, the distal tip segment is thus formed from the base body, the functional elements, and the investment composition.

In order to achieve a high level of reproducibility of the actuation despite the use of an investment composition, it is advantageous when the at least one tension cord has a coating, because such a coating can be designed in such a way that the investment composition is prevented from adhering, in particular during injection molding/vacuum casting of the investment composition. For the same reason, such a coating can be applied to all other components that are encapsulated by the investment composition and are located between the distal counter bearing and the proximal counter bearing (e.g. also on cables, signal lines, and data lines).

Alternatively or in addition, for the same purpose, it can also be provided that a plating envelops the at least one tension cord in the region of the flexible section. As a result, a direct contact of the at least one tension cord with structures outside of the plating can be prevented. In particular, it can thus be prevented that the tension cord cuts into the investment composition during the actuation.

A further advantageous embodiment of the endoscope provides that a torsion-resistant, and preferably kink-resistant, proximal stabilization tube connects proximally to the flexible section and serves as a proximal counter bearing. Here, it is particularly advantageous, for the purpose of simple navigation with the endoscope, when a torsional and/or kink rigidity of the proximal stabilization tube varies in the distal direction, for example decreases or increases.

In this case, it is favorable for the aforementioned plating to have a hardness which is at least 5 times lower than a hardness of the proximal stabilization tube, because this ensures that adjustment forces that are necessary for bending the flexible section are so low that they can be reliably absorbed by the stabilization tube. The advantage of a rigidity of the proximal stabilization tube that changes in the distal direction is also an improved handling and control of the distal end region of the endoscope.

In order to solve the problem mentioned at the outset, the features of the independent method claim are provided according to the invention. In particular, according to the invention, in order to solve the problem in a method of the type described at the outset, it is proposed that a flexible section of the endoscope be formed together with a distal tip segment of the endoscope by means of an investment composition. The distal tip segment can thus comprise numerous components, such as an injection-molded carrier body, electronic components such as image sensors or LEDs, optical fibers, signal lines, etc.; however, the investment composition forms both the tip segment as well as the flexible section of the endoscope at least partially and thus mechanically connects the flexible section to the other components of the tip segment. Thus, part of the tip segment (namely the portion of the investment composition) is formed in one piece with the flexible section.

This investment method using an investment composition can take place, in particular, in such a way that the investment composition extends from the flexible section into the tip segment and/or a proximal counter bearing. As a result, it can be achieved, in particular, that the investment composition also forms the flexible section and at the same time invests an electronic functional element in the tip segment.

Further advantageous embodiments of this production process provide that the endoscope is produced by means of a two-stage casting process, in particular an injection molding process, using an investment composition comprising two different material components. In such a case, for example, the tip segment can be made from a first material component having a greater hardness than a second material component (in each case, of the investment composition).

The investment composition can, however, also be formed, in particular in the flexible section, by means of two different material components, in particular as a two-layer/two-component system. As a result, a preferred position for the angular movement of the tip segment can be achieved.

Another possible embodiment of the method provides that an investment mold used for the production of the endoscope, with which the investment composition is invested, has at least one microstructure or nanostructure, preferably designed as an insert, which is used in order to make an impression of an optical beam-shaping element. This beam-shaping element, which can preferably be arranged in the region of the tip segment, can thus be formed by the investment composition in the investment method by means of the micro/nanostructure, as has already been explained above.

The invention will now be described in more detail on the basis of exemplary embodiments, but is not limited to these exemplary embodiments. Further developments of the invention result from the combination of the features of individual or multiple claims with one another and/or with individual or multiple features of the exemplary embodiments.

BRIEF DESCRIPTION OF THE DRAWINGS

FIG. 1 a plan view from above of an endoscope tip of a flexible endoscope according to the invention;

FIG. 2 a further view of the endoscope from FIG. 1;

FIG. 3 a further view of the endoscope from FIG. 1;

FIG. 32 to FIG. 40 various designs of guide elements, wherein various types of holding devices for the tension cords are shown;

DETAILED DESCRIPTION

Figure 4:
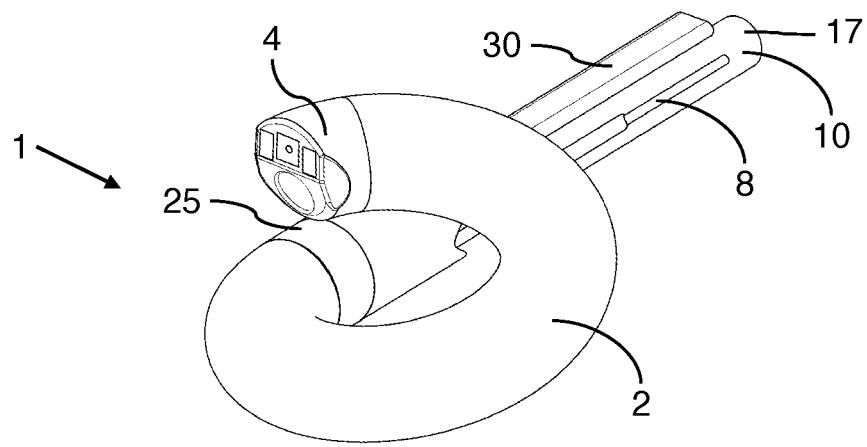
FIG. 4 a further view of the endoscope from FIG. 1.
Figure 5:
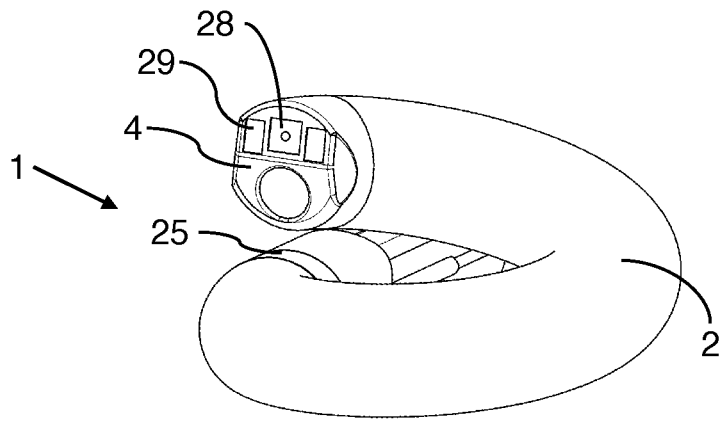
FIG. 5 a further view of the endoscope from FIG. 1.
Figure 6:
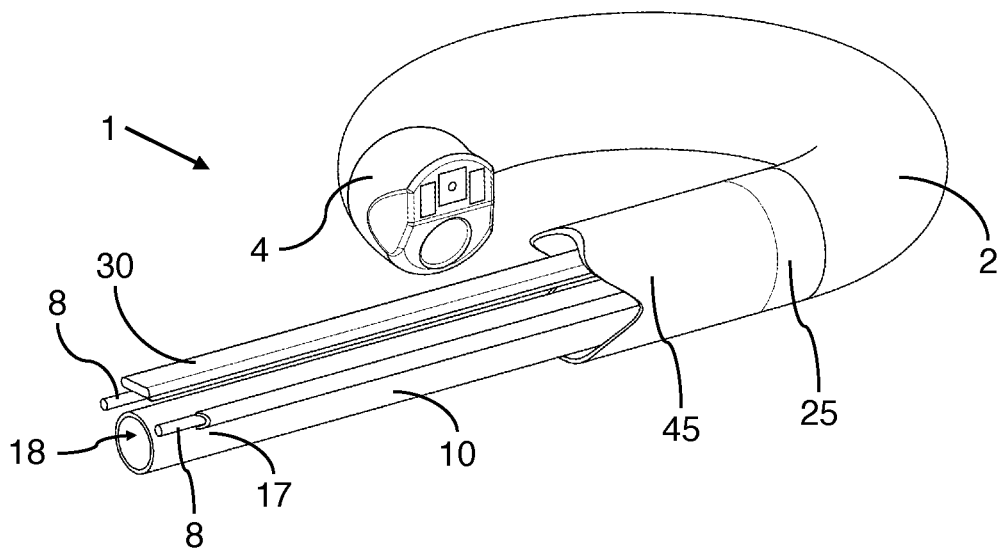
FIG. 6 a further view of the endoscope from FIG. 1.
Figure 7:
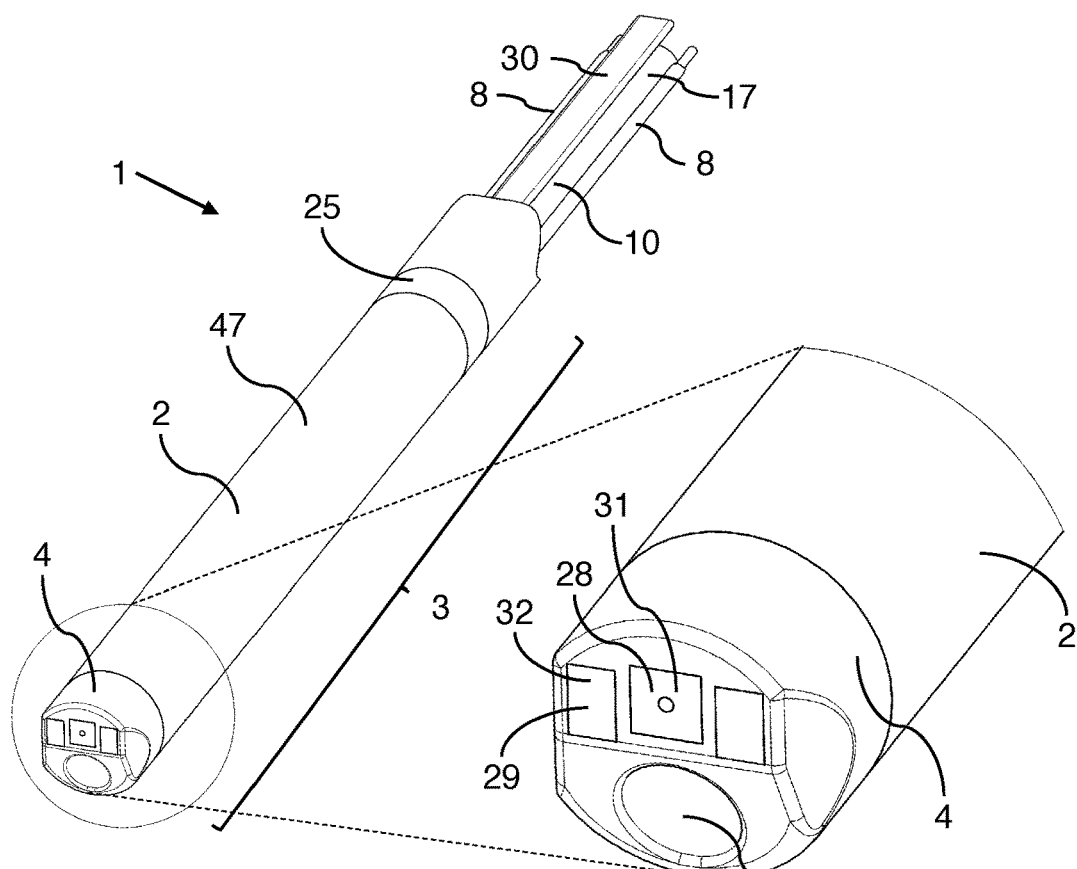
FIG. 7 a further view of the endoscope from FIG. 1 with a fully stretched flexible section and a detailed view of the distal tip segment of the endoscope.
Figure 8:
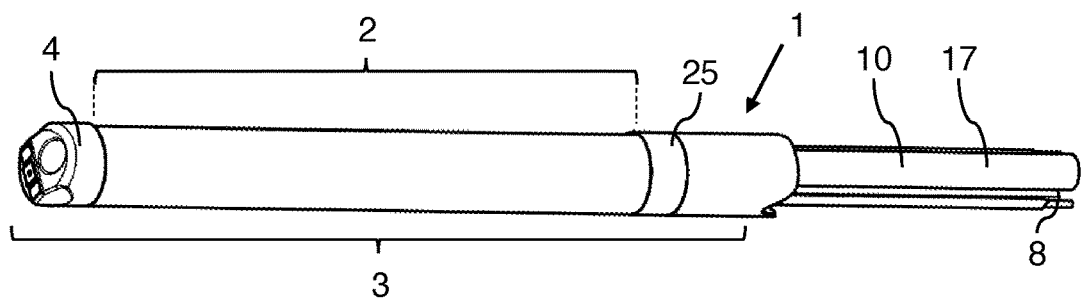
FIG. 8 a further view of the endoscope from FIG. 7.
Figure 9:
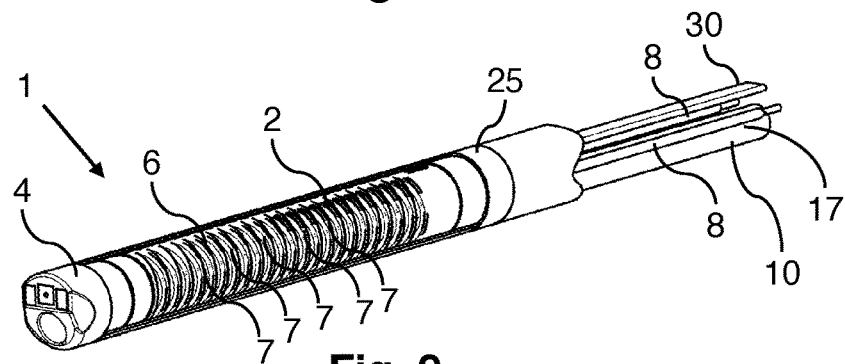
FIG. 9 a further view of the endoscope from FIG. 7, with a enveloping tube removed so that the view of the skeleton below is clear.
Figure 10:
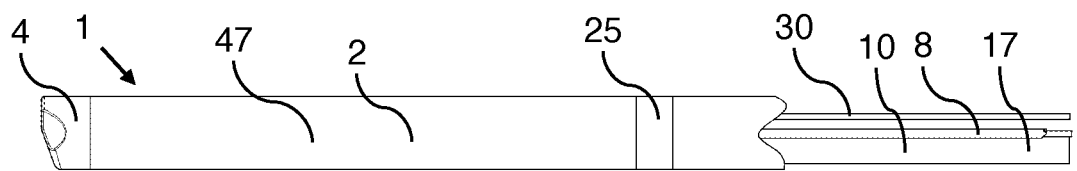
FIG. 10a side view of the endoscope from FIG. 7.
Figure 11:
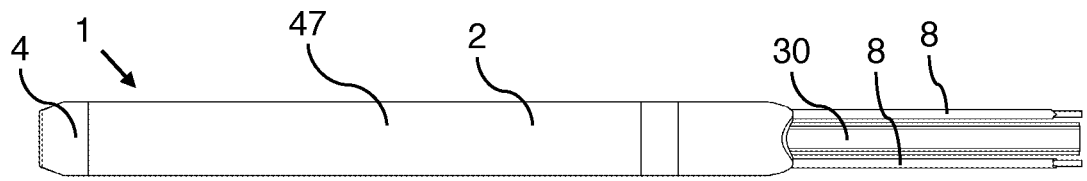
FIG. 11a further side view of the endoscope from FIG. 7.
Figure 12:
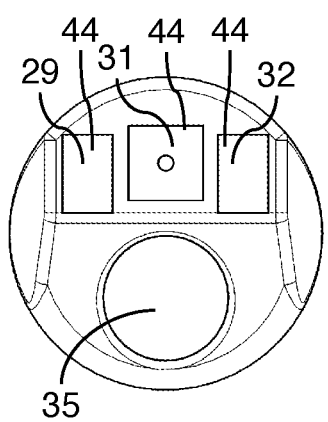
FIG. 12 to FIG. 17 various possible configurations of the tip segment of the endoscope.
Figure 13:
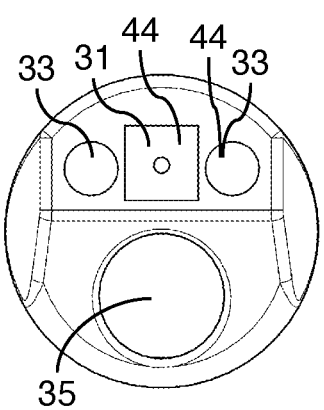
Figure 14:
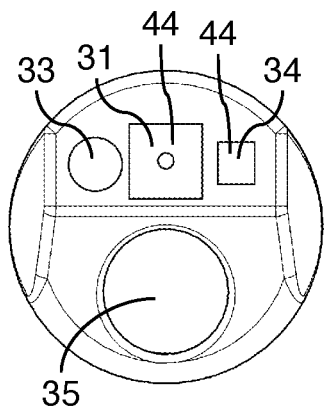
Figure 15:
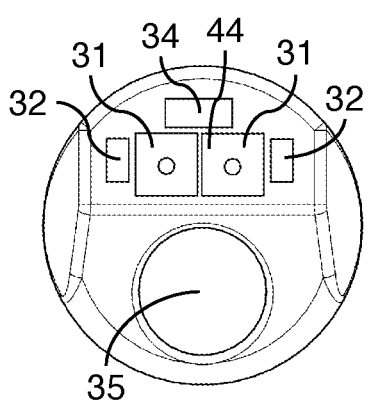
Figure 16:
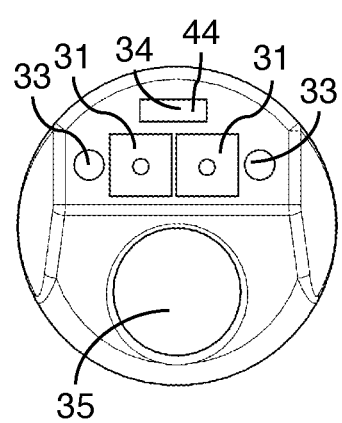

In the following description of various preferred embodiments of the invention, elements with corresponding functions are given the same reference numbers, even if they have a different design or shape. The figures are therefore initially described together, and the differences between the exemplary embodiments are discussed below. The explanations then apply accordingly.

As used herein, the terms "invest," "investing," and "invested," refer to embedding, molding, or otherwise surrounding/containing a component or structure within a material, such as, for example, a component of a flexible endoscope within another component or structure of the endoscope.

The term "investment composition" as used herein refers to a soft, flexible material into which other components or structures may be invested, e.g., molded, embedded or otherwise surrounded by/contained within the material. The investment composition may be a polymer such as silicone, into which, for example, a skeleton 6 of an embodiment, may be molded/embedded, either by injection molding, by a casting process, or by other techniques, such as, for example, processes where the investment composition is initially a liquid and then is solidified into a mass, via UV curing, a curing agent, and the like. As described in greater detail herein, the investment composition may be a single material such as a temperature-curing, one-component silicone, or a multiple component composition such as a two-component epoxy or silicone.

The figures each show the endoscope tip, that is to say a distal end region 3 of a flexible endoscope 1 or parts thereof. The various endoscopes 1 shown are designed to be inserted into the human body or into another cavity (for non-medical applications).

For this purpose, the endoscopes have a flexible section 2, which is arranged in a distal end region 3 of the endoscope 1.

A distal tip segment 4 adjoins the flexible section 2.

The tip segment 4 can be controlled in a manner known per se by means of at least one tension cord 8.

In the embodiments according to the invention, the flexible section 2 has a skeleton 6, which has a large number of guide elements 7. These guide elements 7 guide the tension cords 8 in such a way that their position is fixed transversely to the longitudinal direction of the endoscope 1, that is to say radially, and in the circumferential direction.

For this purpose, the respective tension guides 9 of the guide elements 7 each define a radial position 11 and/or an angular position 12 of the at least one tension cord 8.

Here, the radial position 11 and/or the angular position 12 can be defined in relation to a neutral fiber 13 of the flexible section 2.

The guide elements 7 are lined up, preferably at regular intervals, along the neutral fiber 13, which can define a longitudinal direction of the endoscope 1. However, the distances can also be of different sizes, depending on the configuration.

For simple production, it is preferable for the guide elements 7, as illustrated in the figures, to be designed in order to be identical to one another. However, particularly in the case of endoscopes that allow multiple angulations, it can be useful to assemble guide elements 7 that are not identical, that is, differently configured, in order to form a skeleton 6.

Figure 18:
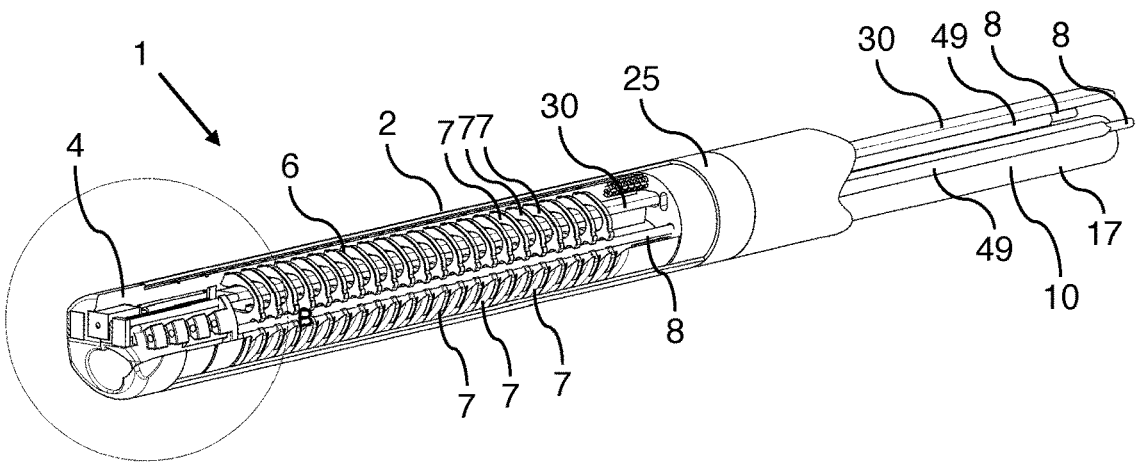
FIG. 18 a partial longitudinal section through the endoscope according to FIG. 1.

The skeleton 6 (e.g. in FIG. 18) is designed as an inner skeleton (i.e. it is not part of an outer shell) and has an axial support structure 10, which is used in order to axially fix the guide elements 7 along a longitudinal axis 16 of the flexible section 2.

The axial support structure 10 has (at least) one support tube 17 with (at least one) internal working volume 18 or (at least one) working channel 35 and forms a flexible core, which—without a working volume—can be designed free of cavities. The working channel 35 can form a receptacle 37 for instruments.

Figure 17:
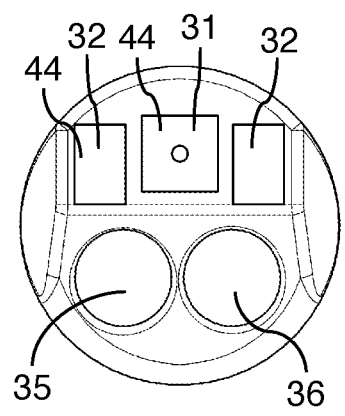

FIG. 17 shows a variant with an additional flushing and/or instrument channel 36. The latter can also be integrated into the working channel 35.

The skeleton 6 is invested into an investment composition 14. This investment composition 14 also forms the flexible section 2 and defines its mobility or flexibility.

In this case, the investment composition 14 fills the interstices 15 between the guide elements 7 at least partially or even completely. The guide elements 7 are thus supported against one another.

The investment composition 14 is vacuum-cast (that is, cast using a negative pressure) or cast in some other way in the interstices of the skeleton 6.

The axial support structure 10 can also be cast, for example with the aid of a first component of a two-component investment composition. This first component can preferably (in the hardened state) be more rigid than a second component of the two-component investment composition. The latter can then form the investment composition 14 described above. As a result, sufficient mechanical stability is achieved by the first component, with simultaneous high flexibility due to the softer second component.

It can be seen from the figures that the guide elements 7 are each designed in the form of discs. The guide elements 7 are designed to be rigid and can stably absorb lateral forces that act on the tension cords 8 when subjected to tension stress.

Figure 19:
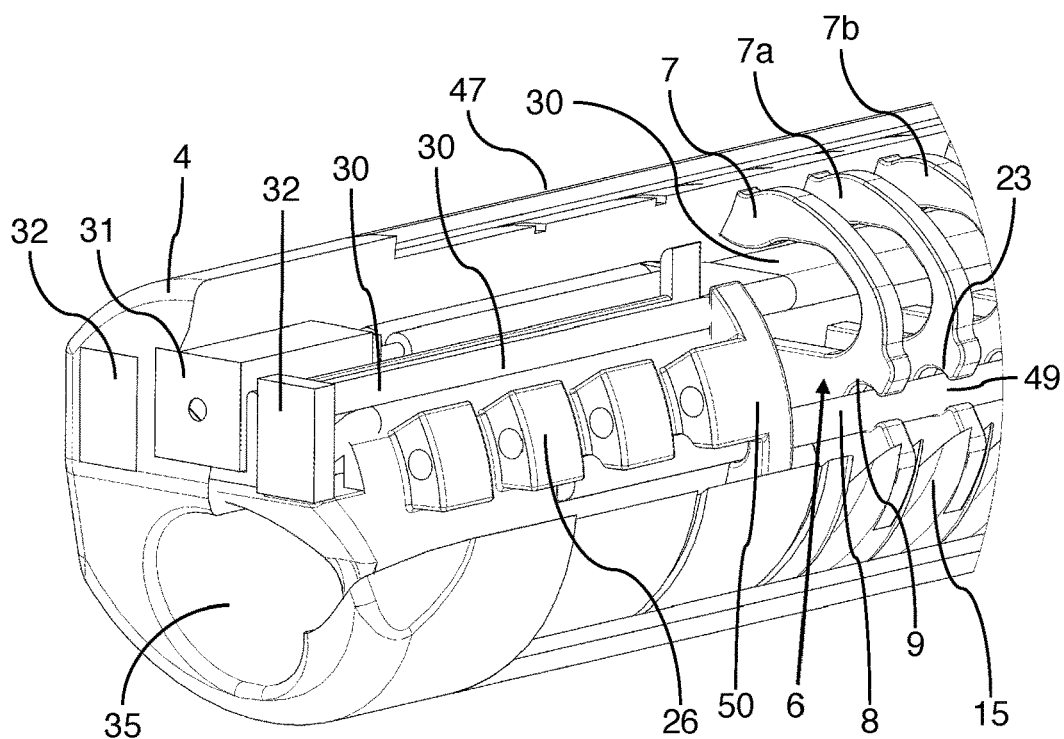
FIG. 19 a detailed view B of the longitudinal section from FIG. 18.
Figure 20:
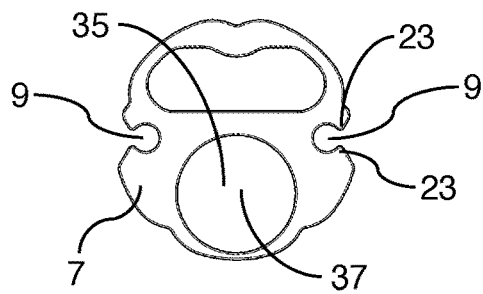
FIG. 20 a single guide element of the skeleton of the endoscope from FIG. 18.
Figure 21:
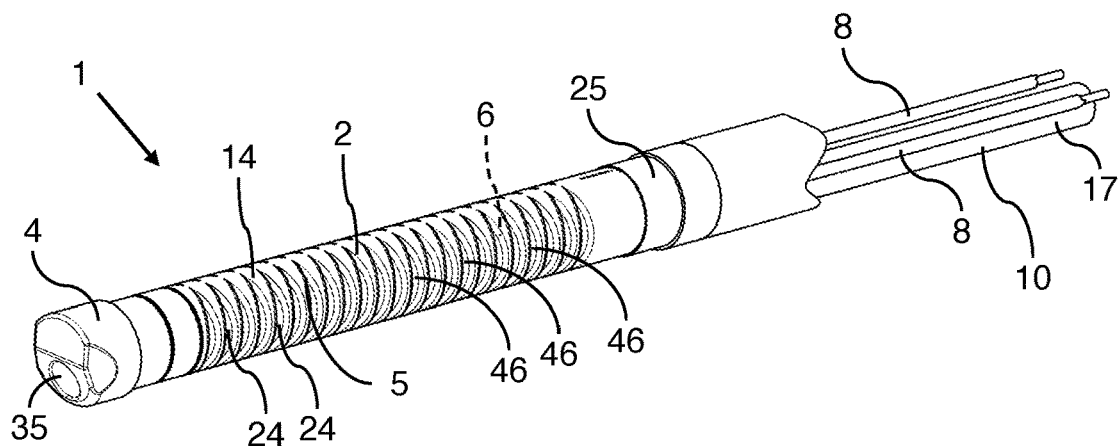
FIG. 21 another view of the endoscope from FIG. 18, this time only with the enveloping tube removed, so that the view of the investment composition underneath, which partially envelops the skeleton, is clear.
Figure 22:
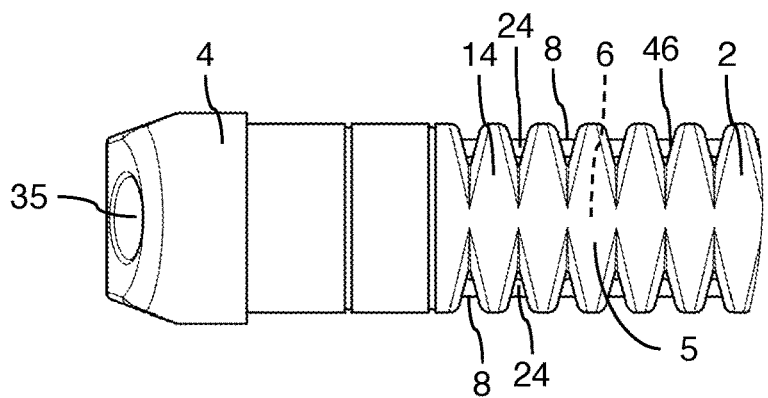
FIG. 22 a detailed view of the view according to FIG. 21, viewed from above.
Figure 54:
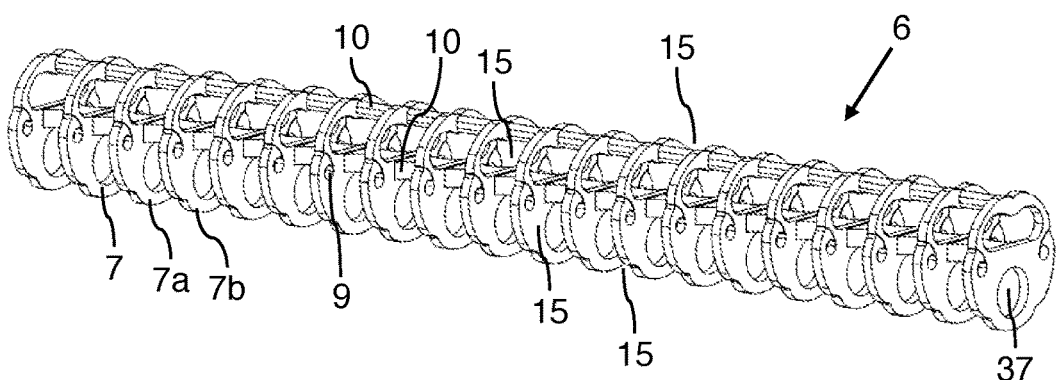
FIG. 54 an example of an endoskeleton according to the invention for an endoscope according to the invention, wherein the skeleton has an axial support structure.
Figure 55:
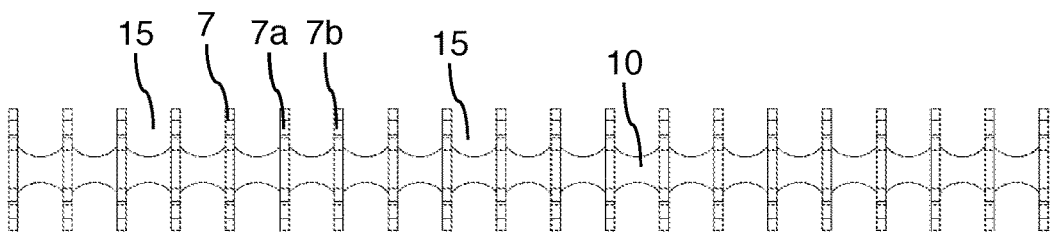
FIG. 55a view from above of the endoskeleton of FIG. 54.
Figure 56:
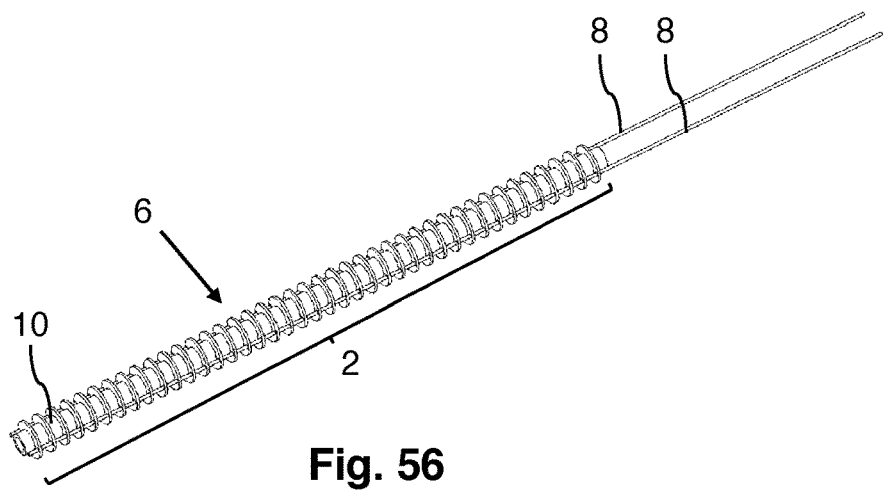
FIG. 56a further example of a skeleton of an endoscope according to the invention.
Figure 57:
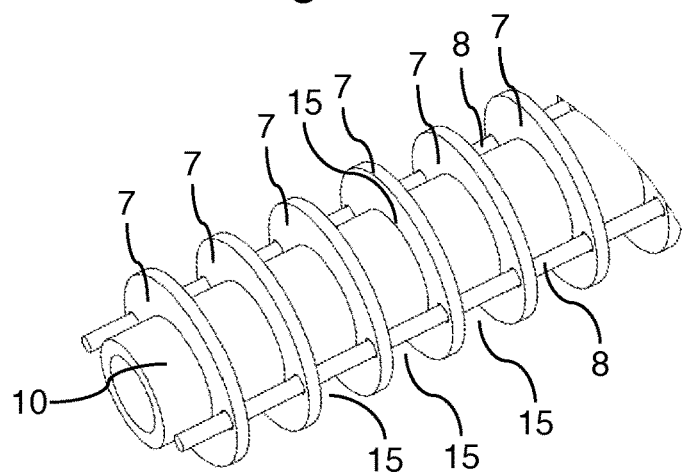
FIG. 57a detailed view of the skeleton from FIG. 56.
Figure 58:
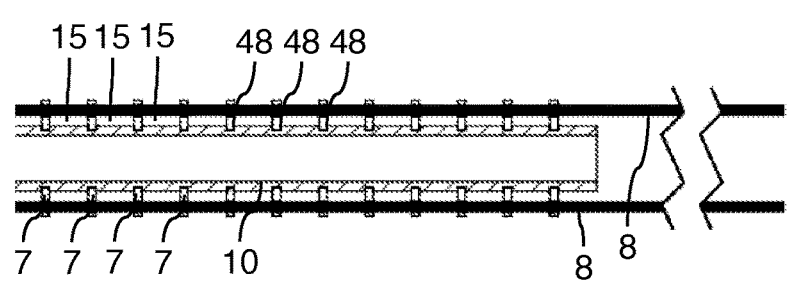
FIG. 58a longitudinal sectional view of the skeleton from FIG. 56.
Figure 59:
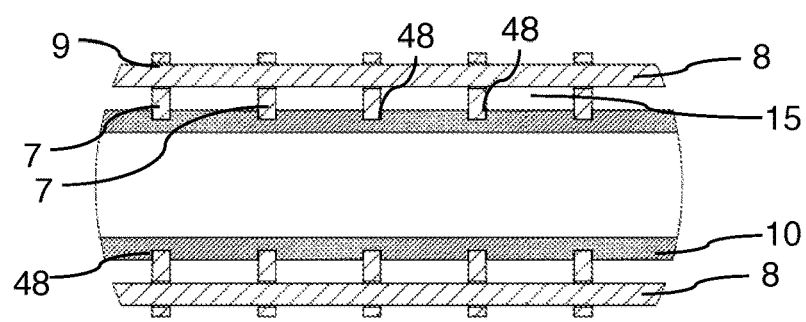
FIG. 59a detailed view of the longitudinal section from FIG. 58 showing the axial fixing of the guide elements on the axial support structure.

As can be seen for example in FIG. 19 or FIG. 54, it is advantageous for a high mechanical stability of the skeleton 6 when guide elements 7a, 7b, which are directly adjacent to one another, are at most as far apart from one another as their respective diameter.

For this purpose, the guide elements 7 lie transversely to a running direction 19 of the at least one tension cord 8, so that the respective tension cord 8 runs transversely through the guide element 7.

The guide elements 7 are thus aligned with a longitudinal axis 16 of the endoscope 1.

It can also be seen from the figures that the guide elements 7 are arranged within the flexible section 2 in order to stabilize it. Here, a distance between directly adjacent guide elements 7a, 7b is less than their respective diameter.

The flexible section 2 is controlled in a manner known per se by tensile and/or compressive stress on the tension cords 8. For this purpose, due to the current shape of the flexible section 2, each tension cord 8 develops lateral forces which can be directed radially inwards or outwards. The guide elements 7 thus each support forces applied radially inwards and/or radially outwards from the tension cords 8 and thus prevent the tension cords 8 from cutting into the investment composition 14 when the tip segment 4 is actuated.

Here, the guide elements 7 do not support the respective tension cord 8 at least at a respective insertion point 20.

Furthermore, the guide elements 7 each form passages 21 for the tension cords 8. The tension cords 8 can thus be introduced from the outside transversely to their respective running direction 19. A threading is therefore not necessary.

In order to absorb the radial forces mentioned, the passages 21 each have support surfaces 22 arranged radially on the outside.

It can be seen that the guide elements 7 are shaped in such a way that the tension cords 8 can each be inserted or hooked into tension guides 9 of the guide elements 7 transversely to a longitudinal axis 16 of the endoscope 1.

For this purpose, a holding device 23 is formed on each of the tension guides 9 in order to prevent the tension cord 8 from escaping from the tension guide 9.

The securing device 23 has a clamping or crimping mechanism (crimping 27), wherein the guide elements 7 are elastically or plastically deformable in the region of the cable guides 9 in order to form the holding device 23.

Between the guide elements 7, there are sections 24 which are not covered by the investment composition 14 (cf. FIGS. 21-23 and 41-43). This reduces friction losses between the at least one tension cord 8 and the investment composition 14 when the tip segment 4 is controlled. The exposed sections 24 thus serve to keep the control forces for the angulation of the tip segment as low as possible and thus enable a particularly smooth angulation.

The flexible section 2 has a plurality of at least partially circumferential indentations 46, which are formed by casting/injection molding the investment composition 14, wherein the indentations 46 follow circular paths or helical lines.

FIGS. 1 to 45 and 50 to 59 show exemplary embodiments with two tension cords 8, 8a, 8b.

Figure 46:
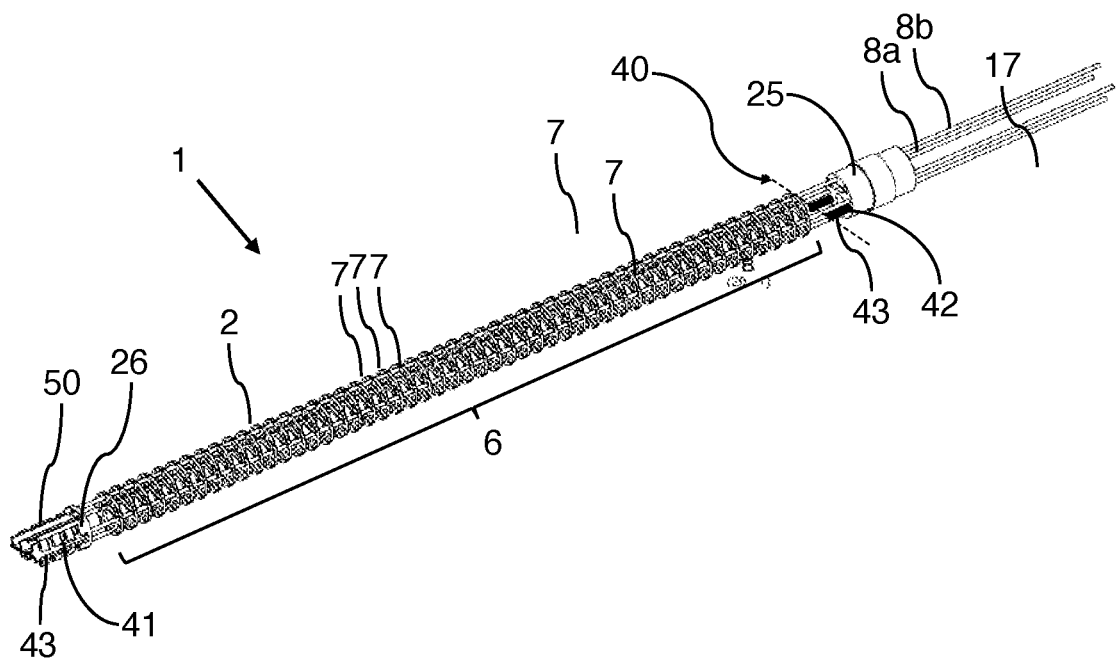
FIG. 46a skeleton of an endoscope according to the invention with four tension cords, designed for 4-fold angulation, before investment in an investment composition.
Figure 47:
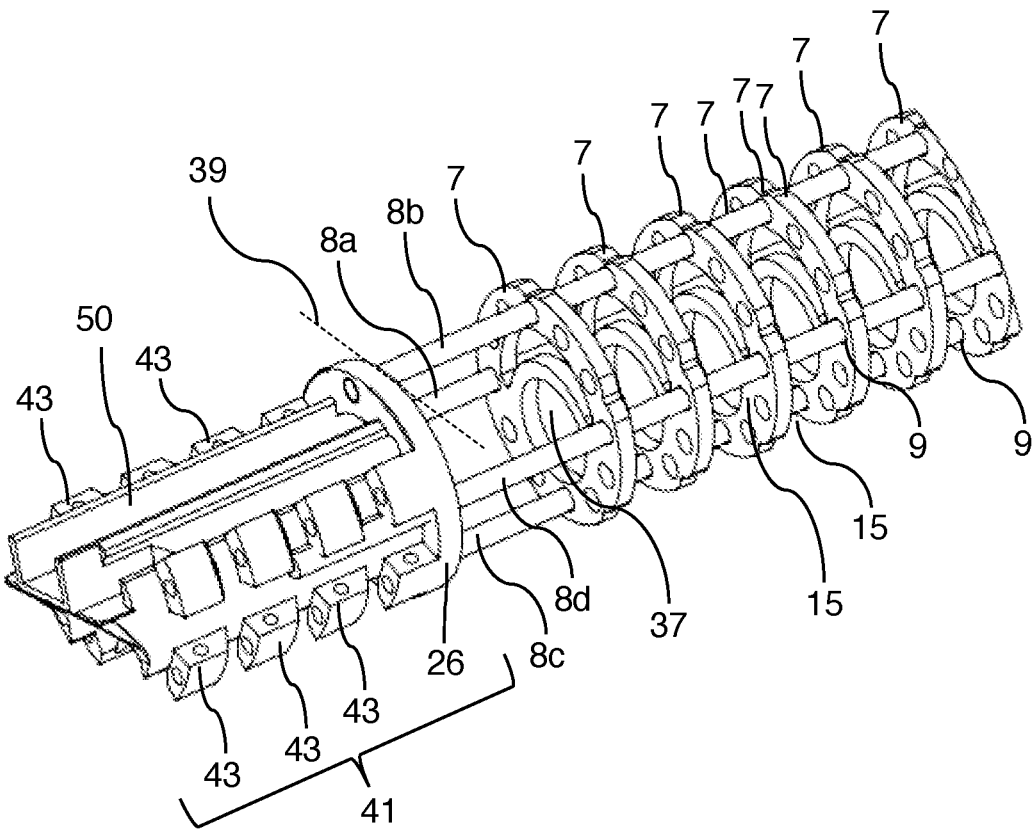
FIG. 47a detailed view of the skeleton from FIG. 46.
Figure 48:
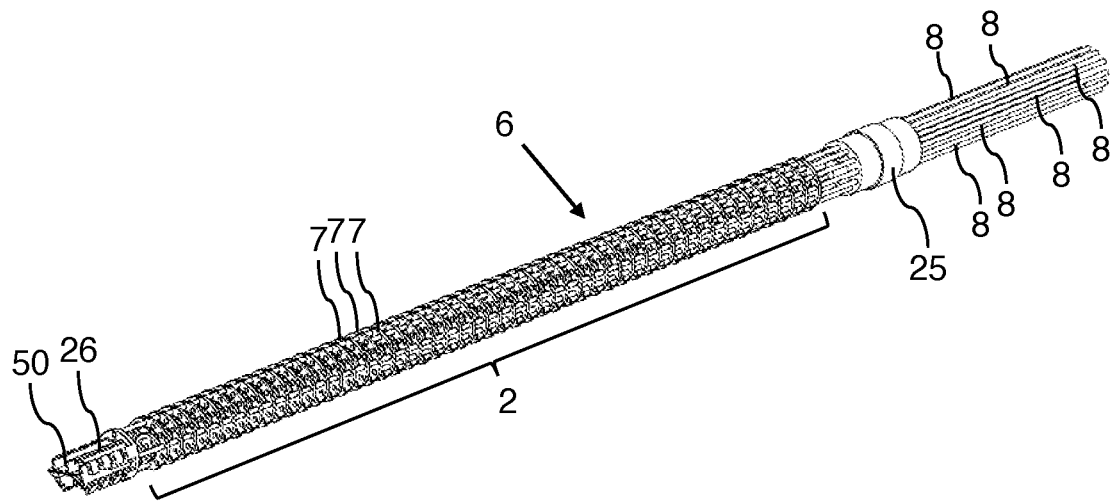
FIG. 48a skeleton of an endoscope according to the invention with a number of more than four tension cords, designed for multiple angulation, before investment in an investment composition.
Figure 49:
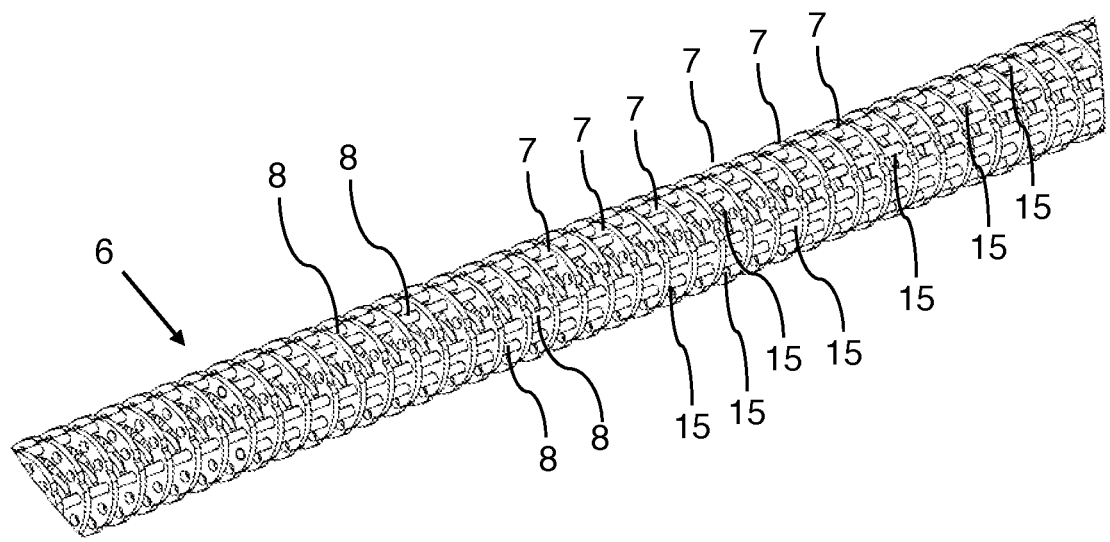
FIG. 49a detailed view of the skeleton from FIG. 48.
Figure 50:
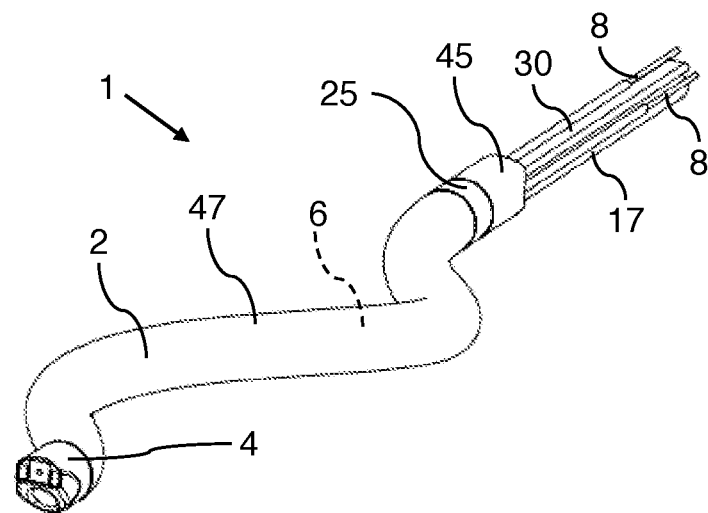
FIG. 50 an illustration of possible angulations of the endoscope from FIG. 46.
Figure 51:
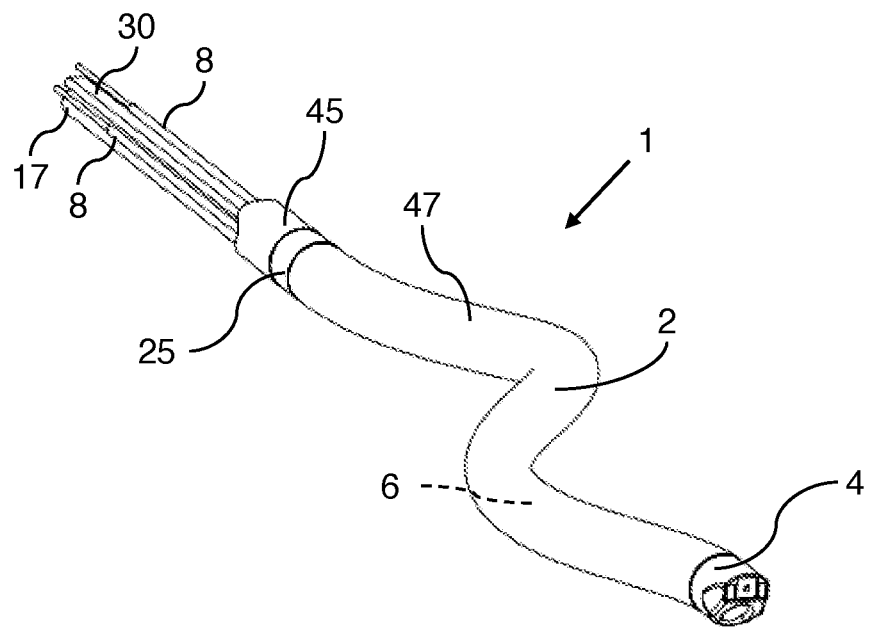
FIG. 51a further illustration of possible angulations of the endoscope from FIG. 46.

FIGS. 46, 47 show an exemplary embodiment with four tension cords 8a, 8b, 8c, 8d, and FIGS. 48 and 49 show an embodiment example with a large number of tension cords 8.

In FIGS. 48 and 49, it can be provided that the tension cords 8 do not all begin or end at the same axial height, for example for a control with multiple different or opposing successive curvatures.

Each of the guide elements guides all existing tension cords 8, 8a, 8b, 8c, 8d, wherein the tension cords 8, 8a, 8b, 8c, 8d are each connected to the distal tip segment 4 of the endoscope 1 and to individual guide elements 7 in a tension-resistant manner.

A possible production or assembly of a flexible endoscope 1 is described below.

For this purpose, a large number of guide elements 7 for guiding at least one tension cord 8 of the endoscope 1 are lined up in order to form a skeleton 6, even before the skeleton 6 is invested into an investment composition 14.

The guide elements 7 are aligned and held in position during investment in the investment composition 14 by an investment mold that is used for this purpose. Before the skeleton 6 is invested in the investment composition 14, each tension cord 8, 8*a*, 8*b*, 8*c*, 8*d* is introduced into tension guides 9 of the guide elements 7 along a longitudinal axis 16 of the endoscope 1. Alternatively, it is also possible to insert each tension cord 8, 8*a*, 8*b*, 8*c*, 8*d* laterally in tension guides 9 of the guide elements 7 transversely to a longitudinal axis 16 of the endoscope 1.

There, it is held in position by means of holding devices 23 formed on the guide elements 7.

The tension cords 8, 8*a*, 8*b*, 8*c*, 8*d* are then each invested in an inserted position of the investment composition 14.

The guide elements 7 are thus lined up in order to form the skeleton 6 by being threaded onto tension cords 8, 8*a*, 8*b*, 8*c* or onto an axial support structure 10.

In FIGS. 12 to 17, a great variety of combinations are shown. For example, lighting and sensor components can be arranged as desired within an encapsulation material. Image sensors 31 can be used as sensors, for example, and/or sensors 34 for pH value, pressure, temperature, magnetic field and/or position in space, in each case with any required reference sensors.

The lighting can be realized, for example, by means of an LED 32, which is arranged either in the tip segment 4 or—if necessary, with lateral irradiation for homogeneous illumination—in the investment composition 14, for example in transparent silicone.

Optical fibers 33, for example glass and/or plastic fibers, can be present with proximal illumination by an LED or a laser—also multispectrally with several wavelengths, for example.

For the lighting, a nanostructure and/or microstructure and/or a recess for molding a lens can also be provided in a casting mold, in particular the casting mold for the skeleton 6. The latter can optimize the illumination and/or project a light grid—for example for structured light measurements or strip light topometry.

Figure 23:
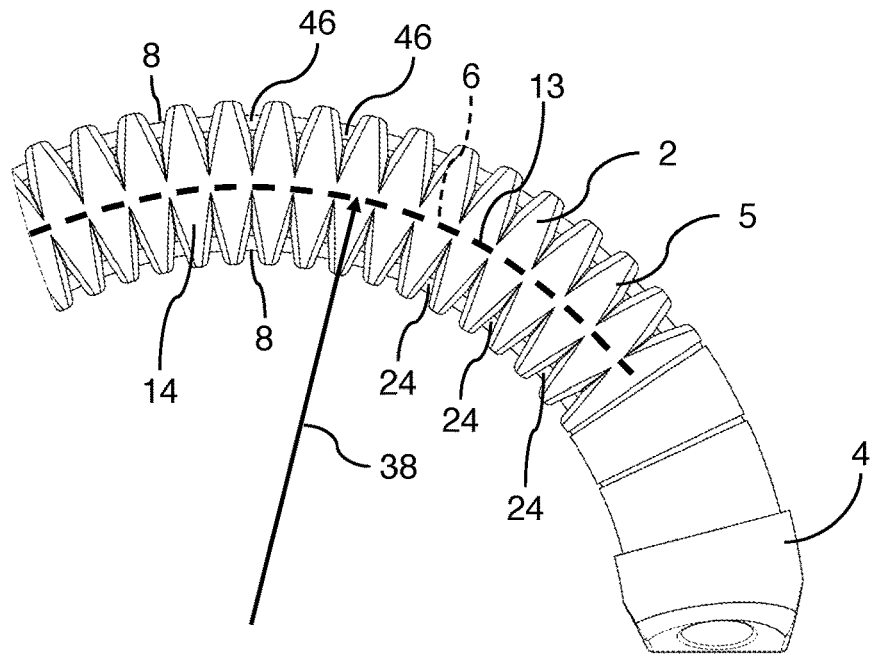
FIG. 23 the endoscope from FIG. 21 in the same view but with an angled flexible section.
Figure 24:
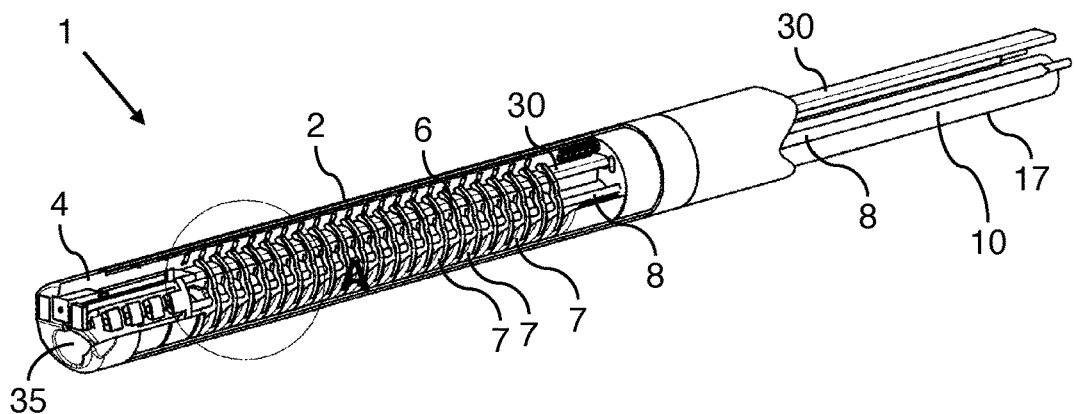
FIG. 24a further endoscope according to the invention in a partial longitudinal sectional view.
Figure 25:
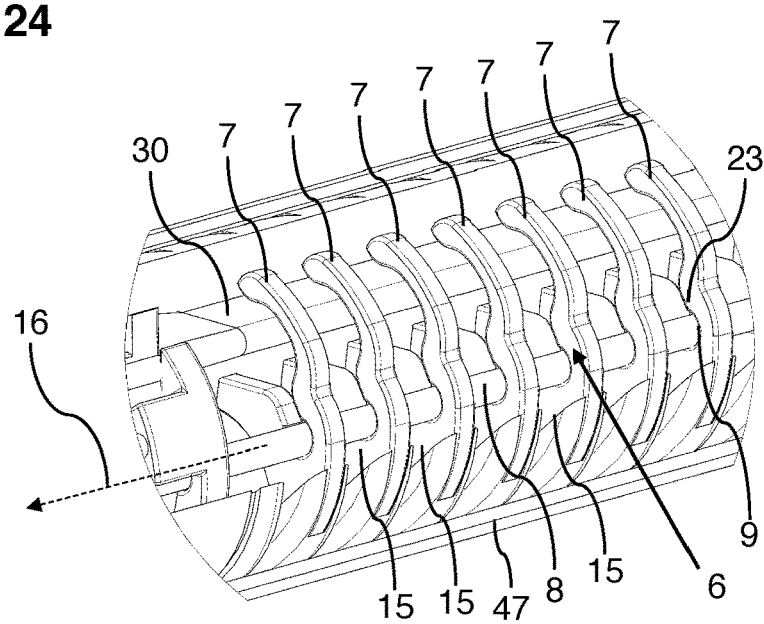
FIG. 25a detail A of the view from FIG. 24.
Figure 26:
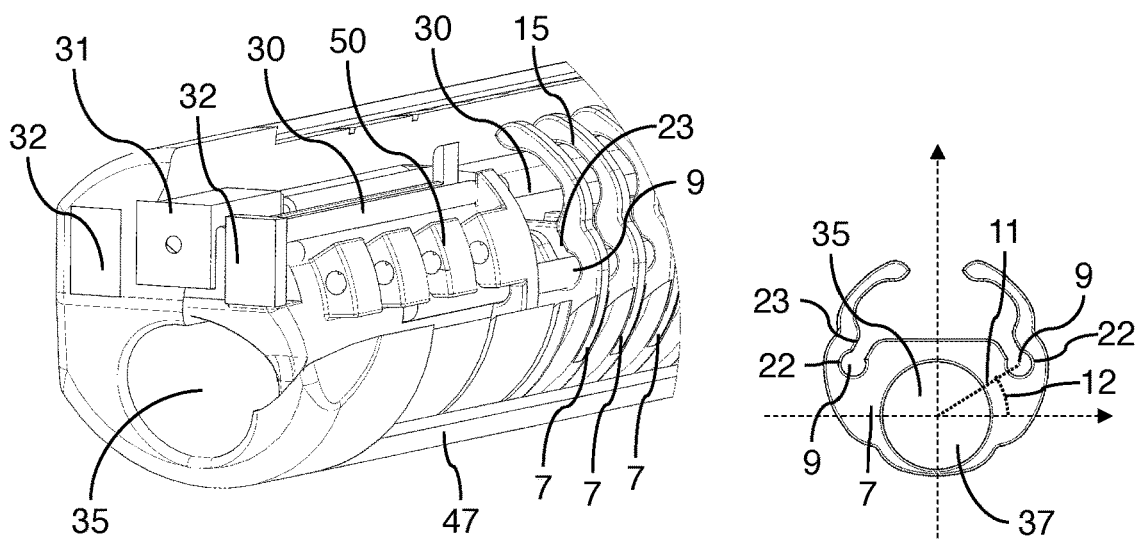
FIG. 26a further detailed view of the endoscope from FIG. 24.
Figure 27:
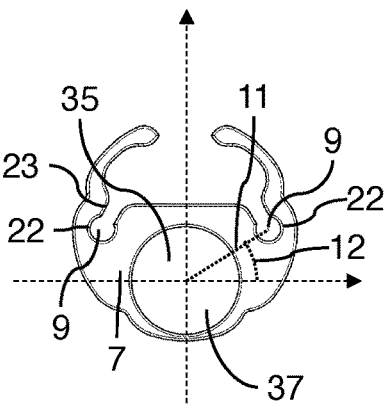
FIG. 27a single guide element of the skeleton of the endoscope from FIGS. 24 and 26, which is designed in such a way that tension cords can be inserted laterally from above into tension guides of the guide element.
Figure 28:
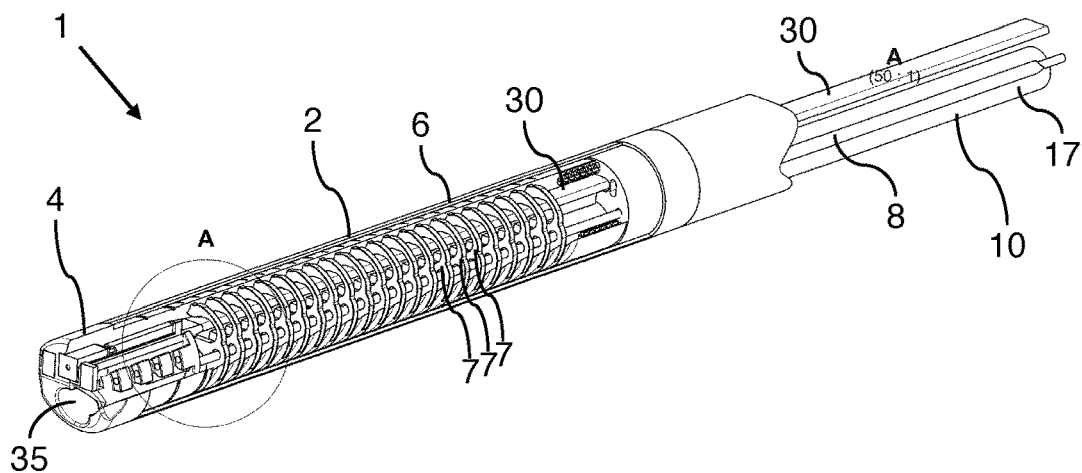
FIG. 28a further endoscope according to the invention in a partial longitudinal sectional view.
Figure 29:
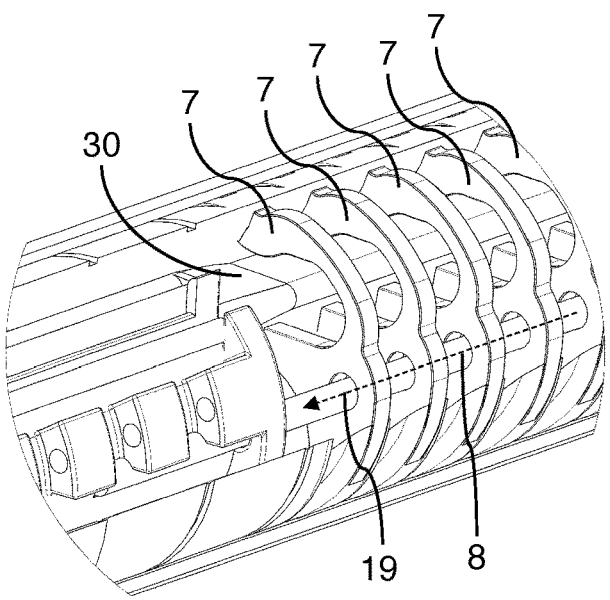
FIG. 29a detail A of the view from FIG. 28.
Figure 30:
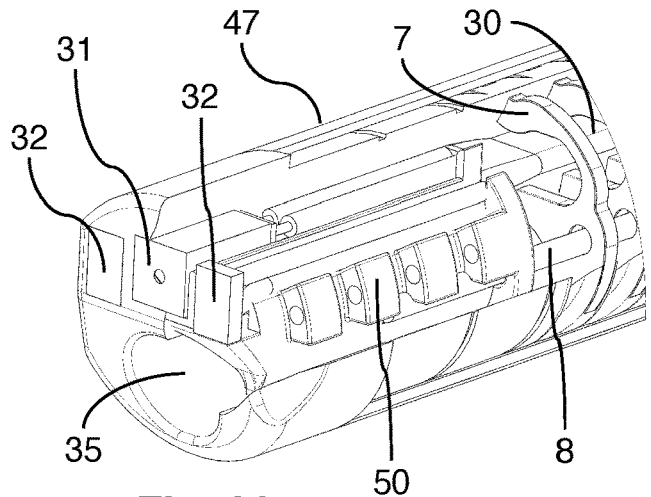
FIG. 30a further detailed view of the endoscope from FIG. 28.
Figure 31:
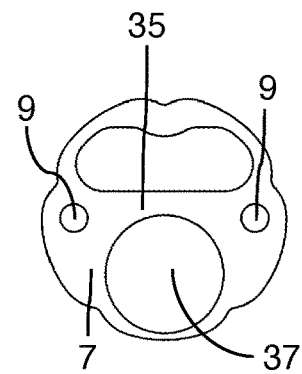
FIG. 31a single guide element of the skeleton of the endoscope from FIGS. 28 and 30, which is designed in such a way that tension cords can be introduced into tension guides of the guide element along a longitudinal axis of the endoscope.

FIG. 23 shows an angled silicone volume with free-standing cables or tension cords 8, which are guided and stabilized by the guide elements 7 in the form of insert rings or ribs.

The silicone composition or investment composition 14 acts between the guide elements 7 as an intervertebral disc. The combination of incised edge structures realized by the casting mold, free-standing tension cords 8, and guide elements 7 enables the smallest possible angulation radii or bending radii 38.

In further exemplary embodiments, instead of or in addition to the proximal anchoring aids or interlocking structures 43, gouged anchoring or interlocking structures are also embodied on the tip segment 4, or at least distally so.

Figure 41:
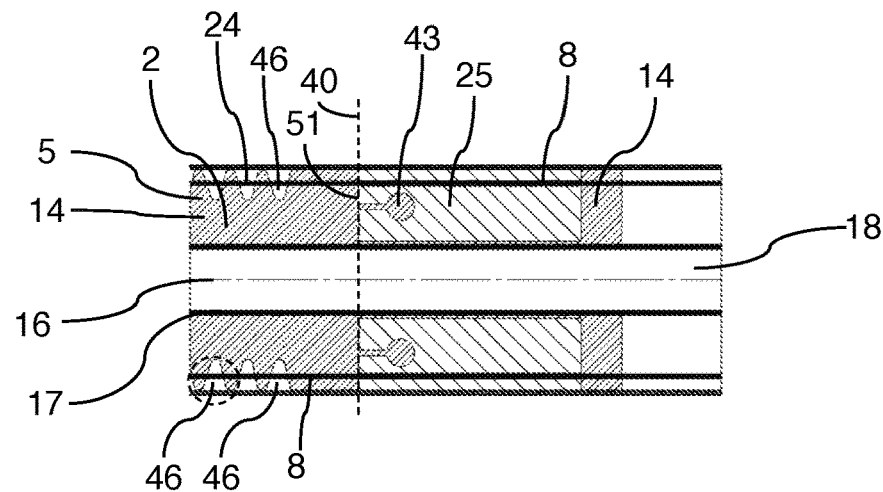
FIG. 41a longitudinal section through the flexible section of an endoscope according to the invention and its anchoring in a proximal counter bearing.
Figure 42:
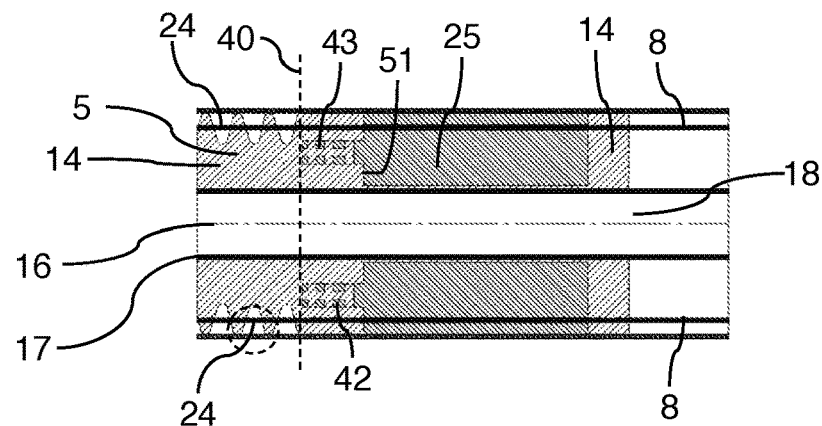
FIG. 42 another possible manner of anchoring a flexible section of an endoscope according to the invention in a proximal counter bearing.
Figure 43:
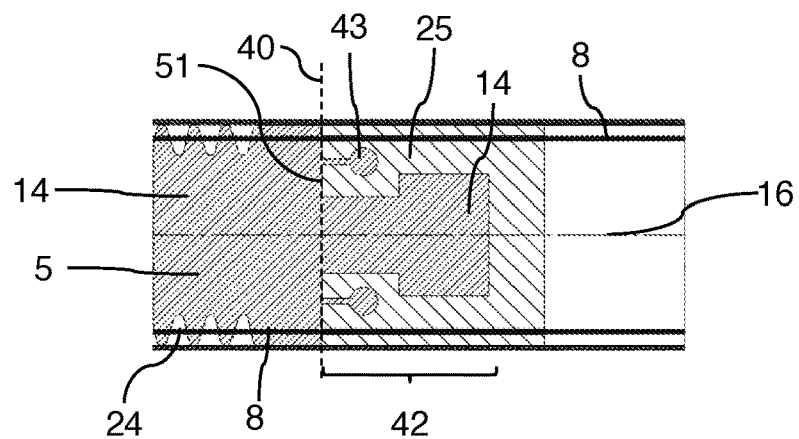
FIG. 43 another possible manner of anchoring a flexible section of an endoscope according to the invention in a proximal counter bearing.

In FIGS. 41 to 43, for example, different gouges can be seen, into which the investment composition 14 can penetrate in order to anchor the flexible section 2.

Figure 52:
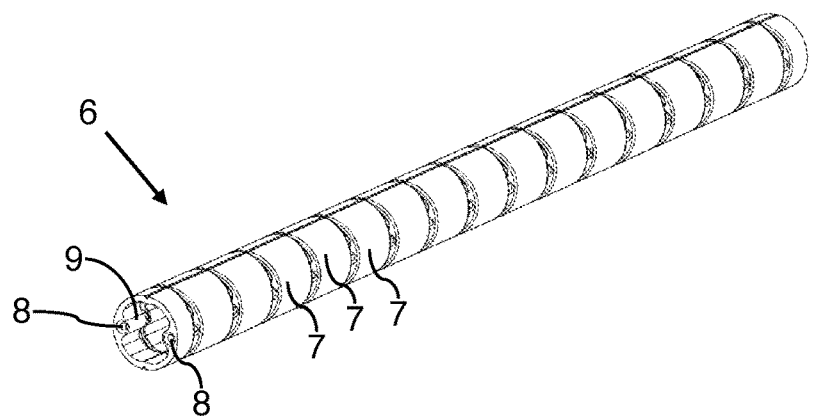
FIG. 52 an example of an exoskeleton according to the invention for an endoscope according to the invention.
Figure 53:
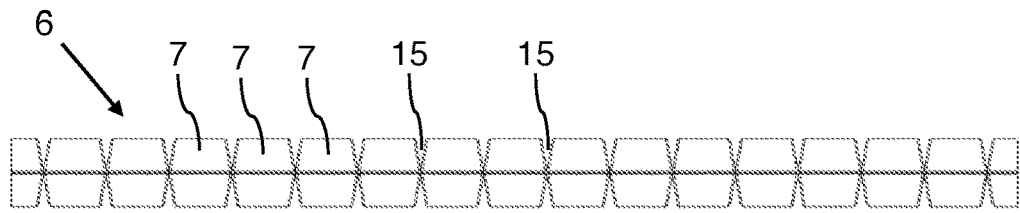
FIG. 53a view from above of the exoskeleton of FIG. 52.

FIG. 52 shows an embodiment with a skeleton 6, which is designed as an exoskeleton.

FIGS. 56 to 59 show a variant in which the guide elements 7 are mounted on a tube structure, for example an elastomer, as individual segments, wherein the guide elements 7 do not touch each other but are held in position by gouges or grooves on the tube structure. These gouges or grooves thus form axial fixings 48 for the guide elements 7.

The interior of the tube structure can be used for the passing of lines and lighting fibers and for flushing or for tools/instruments.

The figures further show that the flexible section 2 is formed by means of an investment composition 14 and that the investment composition 14 is mechanically anchored in the tip segment 4 and a proximal counter bearing 25. The uncontrolled section of the endoscope 1, which is covered by a stabilization tube 45 or a flexible enveloping tube 47, adjoins the counter bearing 25 proximally.

Figure 44:
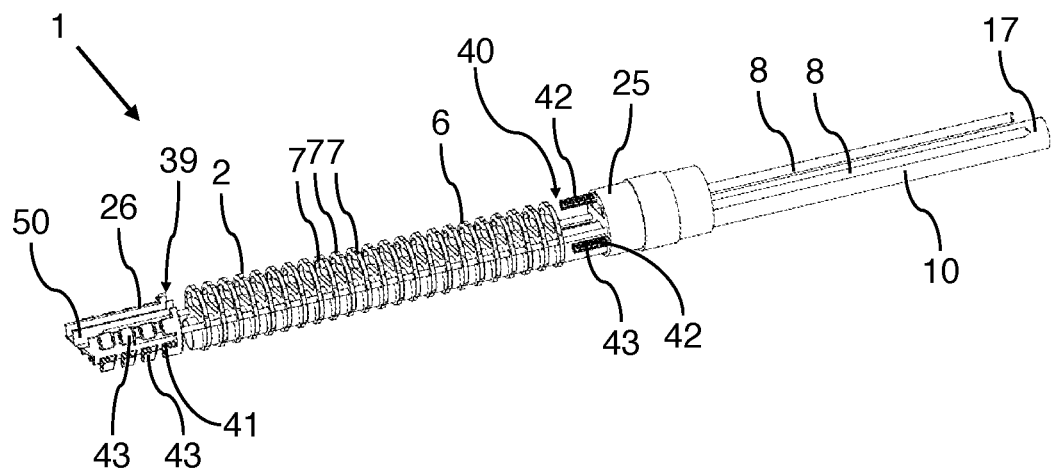
FIG. 44a skeleton of an endoscope according to the invention with two tension cords, designed for a 2-fold angulation, before investment in an investment composition.
Figure 45:
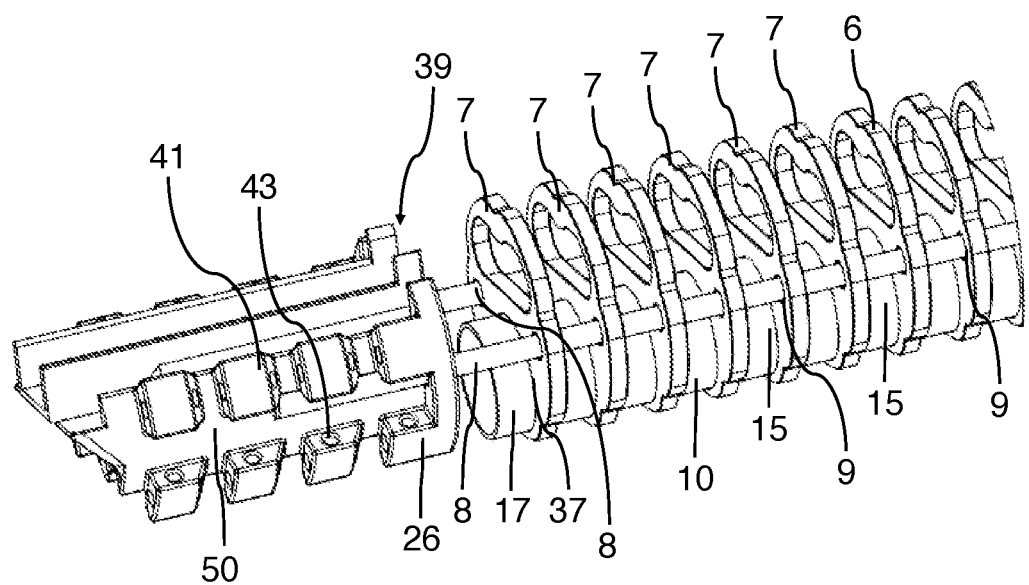
FIG. 45a detailed view of the skeleton from FIG. 44.

Here, the distal tip segment 4 forms a distal counter bearing 26. For this purpose, the tip segment can have a carrier body 50, for example an injection-molded one, as illustrated in FIGS. 44 and 45, which can form distal anchoring aids 41 for anchoring the investment composition 14 and can also carry optical or electronic components such as light sources or sensors. Furthermore, tension cords 8 can also be anchored in the carrier body 50. In addition to the carrier body 50, the distal tip segment can thus comprise electronic and/or optoelectronic components as well as parts of the investment composition 14. Because the distal counter bearing 26 is enclosed by the investment composition 14, it cannot be seen in FIGS. 1 to 6, 10, 11, and 21 to 23.

On the distal tip segment 4, more precisely on the carrier body 50, a proximal end surface 39 is also formed, upon which the flexible section 4 is supported.

The investment composition 14 extends distally beyond the proximal end surface 39. The investment composition 14 thus extends on both sides of the end surface 39.

In the same way, the proximal counter bearing 25 forms a distal end surface 40 upon which the flexible section 4 is supported with its other end.

The flexible section is thus clamped between the end surfaces 39, 40, wherein there exists a tensile stress due to the tension cords 8.

Here, too, the investment composition 14 extends proximally beyond the distal end surface 40 and thus extends on both sides of the end surface 40.

The tip segment 4, more precisely its carrier body 50, forms a distal anchoring aid 41 for anchoring the investment composition 14 in the distal tip segment 4.

The proximal counter bearing 25 also forms a proximal anchoring aid 42 for anchoring the investment composition 14 in the proximal counter bearing 25.

Both the distal anchoring aid 41 and the proximal anchoring aid 42 are implemented in different embodiments by means of a surface treatment and/or by means of an adhesion agent layer and/or by means of interlocking structures 43, such as depressions, gouges, transverse holes, or through-holes.

The distal tip segment 4 also has at least one electronic, in particular optoelectronic, functional element 44, for example a light source 32, 33, an image sensor 31, or some other sensor 34. Signal lines 30 can also be formed to and/or from the functional element 44.

The functional element(s) 44 is/are invested in the investment composition 14 and is/are thus fixed. For this purpose, the investment composition 14 extends without interruption from the tip segment 4 into the flexible region 2.

The investment composition 14 is designed to be transparent or translucent. Thus, light can be received and/or emitted by the electronic functional element 44 through the investment composition 14.

At least one light source, preferably in the form of an LED 32, is invested in the investment composition 14 in the region of the tip segment 4 in such a way that the investment composition 14 serves as an optical fiber and optical diffuser for the light source.

The investment composition 14 invests an optical component, such as an optical fiber 33, in the region of the tip segment 4, or it forms such an optical component.

The investment composition 14 can, for example, form an optical beam-shaping element for shaping beams of illuminating light. The endoscope 1 can thus emit this illuminating light (if necessary, via illuminating optics 29), wherein the investment composition 14 is formed for this purpose by a micro/nanostructure in the region of the optical beam-shaping element.

The tension cords 8, 8a, 8b, 8c, 8d each have a coating that prevents the investment composition 14 from adhering or enables it to be torn away in a controlled manner when used for the first time.

Alternatively, a plating 49 can envelop each tension cord 8, 8a, 8b, 8c, 8d in the region of the flexible section 2 in order to prevent a direct contact of the at least one tension cord 8, 8a, 8b, 8c, 8d with structures outside of the plating 49.

The investment composition 14 is generally elastically deformable and—as mentioned above—transparent for at least one wavelength used for image capturing (possibly via image capturing optics 28) with the endoscope 1 and/or for a wavelength that is emitted as illuminating light by the endoscope.

In a method for producing or assembling one of the flexible endoscopes 1, a flexible section 2 of the endoscope 1 is formed together with a distal tip segment 4 of the endoscope 1 by means of an investment composition 14.

This is done in such a way that, after it has been introduced, the investment composition 14 extends from the flexible section 2 into the tip segment 4 and into a proximal counter bearing 25. The investment composition 14 thus structurally provides a tensile connection between the proximal counter bearing 25 and the distal counter bearing 26 in the tip segment 4.

According to the invention, it is proposed, in the case of an endoscope 1, that an investment composition 14 consisting of a flexible, controllable section 2 be anchored in a counter bearing 25, 26, which forms a support surface 51 for the respective flexible section 2. It is further proposed that a skeleton 6 be formed in a flexible, controllable section 2 with guide elements 7 that are movable relative to one another, each of which guides at least one tension cord 8, 8a, 8b, 8c, 8d laterally. Here, the aforementioned investment composition can support the guide elements 7 of the skeleton 6 against one another.

What is claimed is:

1. A flexible endoscope for insertion into the human body, the endoscope comprising:
   a flexible section arranged in a distal end region of the endoscope, the flexible section comprising a plurality of disc-shaped guide elements that are spaced apart from each other;
   a tip segment distally adjoining the flexible section, said tip segment being controllable by means of at least one tension cord; and
   wherein the flexible section is formed by means of an investment composition that is invested between the guide elements and is mechanically anchored to the tip segment and/or a proximal counter bearing; and
   wherein the investment composition is elastically deformable; and
   wherein the investment composition is mechanically anchored in the tip segment forming a distal counter bearing for the flexible section, and/or in the proximal counter bearing, such that, in either case, the investment composition forms a continuous connection extending over the entire flexible section, and such that the investment composition extends from the flexible section into the tip segment and/or into the proximal counter bearing;
   wherein a carrier body of the tip segment, forms a distal anchoring aid for anchoring the investment composition in the distal tip segment, and/or the proximal counter bearing forms a proximal anchoring aid for anchoring the investment composition in the proximal counter bearing.

2. The flexible endoscope according to claim 1 wherein a carrier body of the tip segment forms a proximal end surface, and the investment composition extends distally beyond the proximal end surface, and/or the proximal counter bearing forms a distal end surface, and the investment composition extends proximally beyond the distal end surface.

3. The flexible endoscope according to claim 1, wherein the distal anchoring aid and/or the proximal anchoring aid are realized by means of a surface treatment, and/or an adhesion agent layer, and/or by interlocking structures.

4. The flexible endoscope of claim 3 wherein the interlocking structures are depressions, gouges, transverse holes, and/or through-holes.

5. The flexible endoscope according to claim 1, wherein the distal tip segment has at least one optoelectronic, functional element, the functional element being a light source, an image sensor, or another sensor, which is at least partially invested in the investment composition and thus fixed, and the investment composition extends without interruption from the tip segment into the flexible region.

6. The flexible endoscope according to claim 5, wherein light is received and/or emitted by the optoelectronic functional element through the investment composition.

7. The flexible endoscope according to claim 1, wherein at least one light source is invested into the investment composition in a region of the tip segment in such a manner that the investment composition acts as an optical fiber and optical diffuser for the at least one light source.

8. The flexible endoscope of claim 7 wherein the at least one light source includes an LED.

9. The flexible endoscope according to claim 1, wherein the investment composition invests or forms an optical component in a region of the tip segment.

10. The flexible endoscope of claim 9 wherein the optical component is an optical fiber.

11. The flexible endoscope according to claim 1, wherein the investment composition forms an optical beam-shaping element for the shaping of a beam of illuminating light that is emitted by the endoscope, out of a micro/nanostructure in a region of the optical beam-shaping element.

12. The flexible endoscope according claim 1, wherein the at least one tension cord has a coating, which prevents the investment composition from adhering, and/or a plating envelops the at least one tension cord in a region of the flexible section in order to prevent a direct contact of the at least one tension cord with structures outside of the plating.

13. The flexible endoscope according to claim 1, wherein the investment composition is transparent for at least one wavelength that is used for image capturing with the endoscope.

14. A method for producing or assembling a flexible endoscope comprising:
   forming a flexible section of the endoscope together with a distal tip segment of the endoscope by means of an elastically deformable investment composition, the flexible section comprising a plurality of disc-shaped guide elements that are spaced apart from each other; and wherein the investment composition extends from the flexible section into the tip segment and/or into a proximal counter bearing; and wherein the investment composition is applied such that the investment composition forms a continuous connection extending over the entire flexible section and thus extends from the flexible section into the tip segment and/or into the proximal counter bearing.

15. The method of claim 14 wherein the investment composition at least partially forms both the distal tip segment as well as the flexible section of the endoscope and mechanically connects the flexible section to other components of the tip segment.

* * * * *